US012622605B2

(12) United States Patent
Karp et al.

(10) Patent No.: US 12,622,605 B2
(45) Date of Patent: May 12, 2026

(54) SMART INFANT MONITORING SYSTEM AND METHOD

(71) Applicant: HB Innovations, Inc., Los Angeles, CA (US)

(72) Inventors: Harvey N. Karp, Los Angeles, CA (US); Peter Fornell, Los Angeles, CA (US)

(73) Assignee: HB Innovations, Inc., Los Angeles, CA (US)

( * ) Notice: Subject to any disclaimer, the term of this patent is extended or adjusted under 35 U.S.C. 154(b) by 552 days.

(21) Appl. No.: 17/696,825

(22) Filed: Mar. 16, 2022

(65) Prior Publication Data

US 2022/0296127 A1 Sep. 22, 2022

Related U.S. Application Data

(60) Provisional application No. 63/161,653, filed on Mar. 16, 2021.

(51) Int. Cl.
| | |
|---|---|
| *A61B 5/11* | (2006.01) |
| *A61B 5/00* | (2006.01) |
| *A61B 5/16* | (2006.01) |
| *G06F 3/14* | (2006.01) |
| *G06V 40/19* | (2022.01) |

(Continued)

(52) U.S. Cl.
CPC ........... *A61B 5/1114* (2013.01); *A61B 5/1118* (2013.01); *A61B 5/163* (2017.08); *A61B 5/4076* (2013.01); *A61B 5/4809* (2013.01); *A61B 5/4812* (2013.01); *A61B 5/6896* (2013.01); *A61B 5/7275* (2013.01); *A61B 5/741* (2013.01); *A61B 5/742* (2013.01); *G06F 3/14* (2013.01); *G06V 40/19* (2022.01); *G10L 25/63* (2013.01); *H04R 1/028* (2013.01); *A61B 2503/04* (2013.01); *A61B 2560/0242* (2013.01); *A61B 2562/06* (2013.01)

(58) Field of Classification Search
CPC .. A61B 5/1114; A61B 5/4809; A61B 2503/04
See application file for complete search history.

(56) References Cited

U.S. PATENT DOCUMENTS

| | | | |
|---|---|---|---|
| 4,958,638 | A | 9/1990 | Sharpe |
| 6,468,234 | B1 | 10/2002 | Van der Loos |
| 2002/0035753 | A1 | 3/2002 | Jakubowski et al. |

(Continued)

FOREIGN PATENT DOCUMENTS

| | | |
|---|---|---|
| AU | 2015264875 | 12/2015 |
| CN | 102164540 | 8/2011 |

(Continued)

OTHER PUBLICATIONS

International Search Report and Written Opinion, issued in PCT/US2022/020656, May 17, 2022.

(Continued)

*Primary Examiner* — Tammie K Marlen

(74) *Attorney, Agent, or Firm* — Blank Rome

(57) ABSTRACT

A sleep system including an analysis unit configured to be in data communication with a plurality of sensors, the sensors being selected from one or more sound sensors, biological sensors, environmental sensors, motion sensors, or a combination thereof.

20 Claims, 5 Drawing Sheets

(51) Int. Cl.

*G10L 25/63*       (2013.01)

*H04R 1/02*       (2006.01)

(56)            References Cited

U.S. PATENT DOCUMENTS

| | | |
|---|---|---|
| 2004/0005088 A1 | 1/2004 | Jeung et al. |
| 2005/0124864 A1 | 6/2005 | Mack |
| 2007/0076935 A1 | 4/2007 | Jeung et al. |
| 2008/0114260 A1 | 5/2008 | Lange et al. |
| 2008/0262381 A1 | 10/2008 | Kolen |
| 2010/0109875 A1 | 5/2010 | Ayon |
| 2010/0241018 A1 | 9/2010 | Vogel |
| 2014/0153794 A1 | 6/2014 | Varaklis et al. |
| 2015/0045608 A1 | 2/2015 | Karp et al. |
| 2015/0094544 A1 | 4/2015 | Spolin |
| 2015/0164409 A1 | 6/2015 | Benson |
| 2015/0208920 A1 | 7/2015 | Ziganshin |
| 2017/0164900 A1 | 6/2017 | Johnson et al. |
| 2017/0164906 A1 | 6/2017 | Ramanan |
| 2017/0215772 A1 | 8/2017 | Garn et al. |
| 2018/0035082 A1* | 2/2018 | Patil ........................ A61B 5/45 |
| 2018/0361263 A1 | 12/2018 | Boeckle |
| 2019/0053757 A1 | 2/2019 | Cooper et al. |
| 2019/0133499 A1 | 5/2019 | Auerback |
| 2019/0139389 A1 | 5/2019 | White |
| 2019/0150798 A1 | 5/2019 | Glazer |
| 2019/0247611 A1 | 8/2019 | Karp et al. |
| 2019/0320974 A1 | 10/2019 | Alzamzmi et al. |
| 2020/0397349 A1 | 12/2020 | Fornell |

FOREIGN PATENT DOCUMENTS

| | | |
|---|---|---|
| CN | 202568219 | 12/2012 |
| CN | 106170229 | 11/2016 |
| CN | 106456053 | 2/2017 |
| CN | 107874761 | 4/2018 |
| CN | 109380777 | 2/2019 |
| CN | 105025790 | 10/2019 |
| EP | 1371042 | 5/2005 |
| KR | 101798498 | 11/2017 |
| WO | 2019049137 | 3/2019 |
| WO | 2020193842 | 10/2020 |

OTHER PUBLICATIONS

Examination Report, CA 3,211,219, Nov. 8, 2025.

Examination Report, AU 2022237542, May 10, 2024.

Extended European Search Report, EP 22772178.4, Dec. 4, 2024.

Examination Report, CA 3,141,932, Jan. 31, 2025.

International Search Report and Written Opinion, PCT/US2020/038477, Sep. 14, 2020.

Brown, The Piezo Solution for Vital Signs Monitoring, Medical Design Tech., pp. 36, Mar. 2008.

Stanford Children's Hospital, Breathing Probllems, www.stanfordchildrensorg/en/topic/default?d=breathing-problems-90-P02666, printed Nov. 12, 2020.

Piezo Solution for Vital Sign Monitoring, TE Connectivity, www.te.com/usa-en/trends/connected-life-health-tech/piezo-solution-for-vital-signs-monitoring.html, printed Nov. 19, 2020.

\* cited by examiner

Sound Sensors 110 microphone 110a

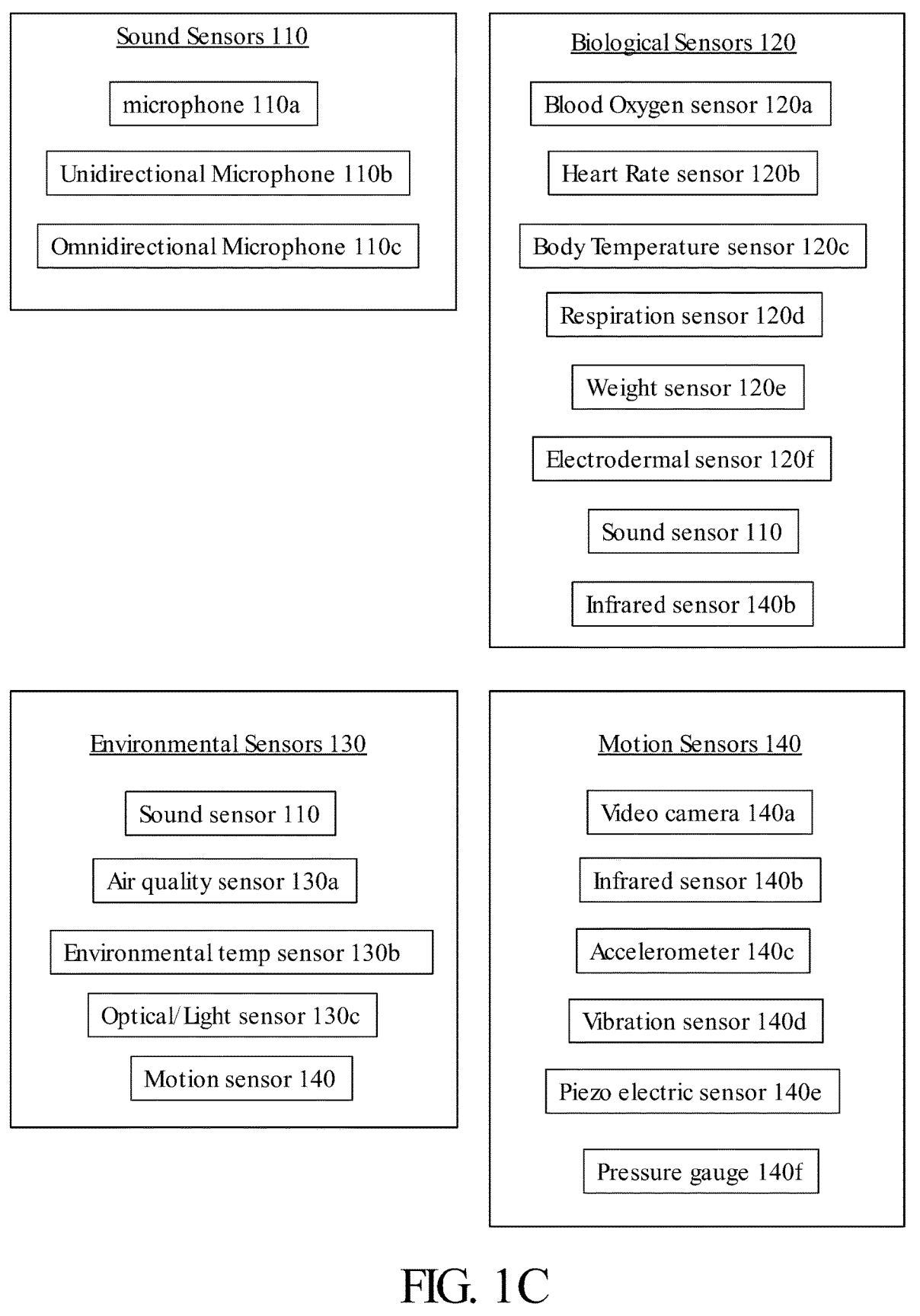

Unidirectional Microphone 110b

Omnidirectional Microphone 110c

Biological Sensors 120

Blood Oxygen sensor 120a

Heart Rate sensor 120b

Body Temperature sensor 120c

Respiration sensor 120d

Weight sensor 120e

Electrodermal sensor 120f

Sound sensor 110

Infrared sensor 140b

Environmental Sensors 130

Sound sensor 110

Air quality sensor 130a

Environmental temp sensor 130b

Optical/Light sensor 130c

Motion sensor 140

Motion Sensors 140

Video camera 140a

Infrared sensor 140b

Accelerometer 140c

Vibration sensor 140d

Piezo electric sensor 140e

Pressure gauge 140f

FIG. 1C

SMART INFANT MONITORING SYSTEM AND METHOD

CROSS-REFERENCE TO RELATED APPLICATIONS

This application claims priority benefit to U.S. Provisional Application No. 63/161,653, filed Mar. 16, 2021, which is incorporated herein by reference in its entirety.

TECHNICAL FIELD

This disclosure generally relates to monitoring infants to collect biological, environments, and/or situational data and analyzing the same. In disclosed embodiments, such collected data may be analyzed to identify psychological, physiological, or various medical conditions.

BACKGROUND

Crib death or SIDS (Sudden Infant Death Syndrome) is a leading cause of infant mortality. Approximately 2400 US infants die each year from SIDS during the first year of life. The peak occurrence is from 2-4 months of age, with 80% of the victims being under 4 months and 90% being under 6 months of age.

While the exact cause of SIDS is unknown, the primary cause is believed to be immaturity of the breathing regulatory system in the brain. In essence, it seems that infants "forget" to breath and their internal alarm system does not reliably arouse them to recommence breathing. Once breathing stops, the body becomes more and more hypoxemic and acidotic, leading to a downward spiral of reduced heart rate, dropping blood pressure, cardiovascular collapse and death.

In the hospital setting, the use of an infant monitor immediately alerts the healthcare workers if an infant stops breathing. The health care workers can often resuscitate the infant with simple stimulation (e.g. vigorous jiggling), without the need of oxygen or formal CPR. However, in the home setting where such medical monitoring equipment may be unavailable, the need exists for a way to detect if infant breathing has stopped so that a corrective action can occur before the onset of serious adverse health effects or SIDS. By intervening as soon as possible after an infant's breathing has stopped, it may become possible to reduce the occurrence of SIDS and further lower infant mortality rates.

Language development is an acquired skill and infant communication is limited to more primal or generalized mechanisms that relay how an infant feels. For example, infants may cry, kick, or toss when upset. But determining the reason as to why an infant is upset is often a matter of educated guessing.

SUMMARY

In various embodiments, an infant analysis system includes a plurality of sensors positioned relative to a sleep device to collect data with respect to an infant when positioned within the sleep device and an environment around the infant. The plurality of sensors include a sound sensor and a motion sensor.

In a first aspect, the system includes a sound analysis module configured to analyze the sound data. The sound analysis module may be configured to identify characteristics and patterns of the sound data alone or together with non-sound data.

In a first configuration, the sound analysis module is configured perform a cry analysis that includes analysis of the sound data corresponding to cries for characteristics to identify nuances and/or emotional factors related to the infant including grunting.

In one example, the cry analysis includes correlation of the sound data corresponding to cries with data collected by the plurality of sensors including motion data, vitals data, environmental data, sleep cycle data, wake/sleep data, or combination thereof.

In the above or another example, the cry analysis utilizes artificial intelligence (AI) or machine learning (ML) model to unwrap the nuances of the cries of the infant.

In any of the above or another example, the sound analysis module may utilize data and/or analysis performed by one or more additional modules selected from a motion analysis module, vital analysis module, weight analysis module, environmental analysis module, evaluation module, sleep state analysis module, or combination thereof. In a further example, the sound analysis module associates with the evaluation module and/or condition identification module to provide sound data or analyses thereof according to an evaluation program and/or for identification of a condition.

In any of the above or another example with respect to the cry analysis, the sound analysis module is configured to analyze sound data corresponding to cries for patterns therein.

In any of the above or another example with respect to the cry analysis, the analysis may further comprises correlating the sound data corresponding to cries or patterns therein with collected data related to vital states, conditions, evaluations, motion/movement, feeding, weight, environment, wake/sleep or sleep cycle data, or combinations thereof.

In any of the above or another example with respect to the cry analysis, the sound analysis module may be is configured to perform a cry analysis that includes analysis of characteristics of cries detected by one or more sound sensors.

In any of the above or another example with respect to the cry analysis, the sound data corresponding to cries is input into the model filtered or raw.

In any of the above or another example with respect to the cry analysis, characteristics of the sound data analyzed includes amplitude, frequency, wavelength, duration, or combination thereof. In a further example, characteristics of the sound data analyzed includes sound patterns, cadence, or both.

In any of the above or another example with respect to the cry analysis, the analysis is configured to distinguish between whether the infant is hungry, unwell/ill, uncomfortable, content, satiated, bored, or tired.

In any of the above or another example with respect to the cry analysis, the analysis starts with a baseline cry to differentiate between cries and grunts.

In any of the above or another example with respect to the cry analysis, the sound analysis module generates a cry algorithm that is personalized to the infant.

In any of the above or another example with respect to the cry analysis, the algorithm is configured to identify values or value ranges in measured characteristics based on previous analyses that are specific to the infant and its behavior states.

In any of the above or another example with respect to the cry analysis, the cry analysis further includes analysis of motion data, weight data, vital data, or combinations thereof. In a further example, analysis of motion data may include identification of intensity kicking or other motions useful for calculating behavior state in conjunction with the sound analysis.

In any of the above or another example with respect to the cry analysis, the cry analysis includes comparing current cries to previous cry analyses to determine if similar grunting sounds have been associated with one or more levels of hunger states, sleep states, tired states, content states, bored states, unwell states, or other behavioral states in previous analyses.

In any of the above or another example with respect to the cry analysis, the cry analysis outputs a predictive smart response for output from a sleep device, peripheral, or combination thereof. In one example, the smart response is configured to transition the infant to or otherwise achieve a desired behavior state.

In any of the above or another example with respect to the cry analysis, a motion analysis module to analyze collected data related movement of an infant. In one example, the movement corresponds to leg movement, eye movement, arm movement, body movement, or head movement. In the above or another example, the movement corresponds to movement of feet, toes, mouth, hands, or fingers. In either of the above or another example, the analysis includes analyzing rate, duration, pattern, and/or distance of movement of one or more of the movements. In any of the above or another example, the analysis of the motion data includes inputting the motion data or both the motion data and non-motion data into an AI scheme to generate a predictive output.

wherein the motion analysis module utilizes data and/or analysis performed by one or more additional modules selected from a sound analysis module, vital analysis module, weight analysis module, environmental analysis module, evaluation module, sleep state analysis module, or combination thereof.

In a second aspect, alternatively or in addition to the first aspect or any configuration or examples thereof, the system includes a vital analysis module configured to analyze collected vital data related body temperature, pulse rate, respiration rate, and/or blood pressure of an infant. In one example, the analysis of the vital data includes inputting the vital data or both the vital data and non-vital data into an AI scheme to generate a predictive output. In this or another example, the vital analysis module utilizes data and/or analysis performed by one or more additional modules selected from a sound analysis module, motion analysis module, weight analysis module, environmental analysis module, evaluation module, sleep state analysis module, or combination thereof.

In a third aspect, alternatively or in addition to the any of the first or second aspects or any configurations or examples thereof, the system may include an environmental analysis module to analyze collected environmental data related to one or more of ambient or non-infant sounds, motion within a surrounding environment, lighting, air quality, air movement, temperature, or other environmental state surround the infant. In one example, the analysis of the environmental data includes inputting the environmental data or both the environmental data and non-environmental data into an AI scheme to generate a predictive output. In the above or another example, the environmental analysis module utilizes data and/or analysis performed by one or more additional modules selected from a sound analysis module, motion analysis module, weight analysis module, vital analysis module, evaluation module, sleep state analysis module, or combination thereof.

In a fourth aspect, alternatively or in addition to the any of the first through third aspects or any configurations or examples thereof, the system includes a weight analysis module configured to analyze collected and/or input weight data of an infant.

In one example, weight data is collected by a weight gauge integrated with a sleep device supporting the infant.

In the above or another example, the analysis of the weight data includes inputting the weight data or both the weight data and non-weight data into an AI scheme to generate a predictive output.

wherein the weight analysis module utilizes data and/or analysis performed by one or more additional modules selected from a motion analysis module, sound analysis module, vital analysis module, environmental analysis module, evaluation module, sleep state analysis module, or combination thereof.

In any of the above or another example, analyzed weight data is output in a report to caregivers to help track weight changes over time.

In a first configuration that may be alternative to or include any of the above examples, the weight data is analyzed to determine a feeding state that includes comparison of current weight data to previously collected weight data to determine if the infant is underfed, overfed, or properly fed and/or satiated. In one example, the analysis considers other data collected such as sleep duration, sleep quality, or behavior state associated with previous weight measurements. In the above or another example, the analysis compares the weight data to a weight pattern, general or personalized weight profile, or threshold values.

In a second configuration that may be alternative to or include any of the above examples, the weight data is analyzed to better understand feeding patterns. In one example, the analysis includes monitoring weight throughout the day over multiple days. In a further example, the analysis includes consideration and/or identification of feeding patterns. In the above or another example, the analysis further comprises correlating an above with sleep patterns.

In any of the above or another example, results of the weight analysis is used to generate an output to a caregiver comprising advice regarding feeding times and/or quantity of food to be fed to the infant.

In any of the above or another example, the weight analysis is used as a health indicator and/or for early diagnosis of health issues.

In any of the above or another example, the weight analysis is used as an indicator of motion data corresponding to distress, sleep state, or to predict or identify instances of sudden infant death syndrome (SIDS).

In a fifth aspect, alternatively or in addition to the any of the first through fourth aspects or any configurations or examples thereof, the system includes an evaluation module configured to analyze collected data according to an active data collection scheme.

In one example, the active data collection scheme comprises a pre-defined evaluation programs designed to evaluate the infant.

In the above or another example, the active data collection scheme comprises an evaluation program intuitively based on analysis of collected data by one or more analysis modules and/or modeling engine that self-evolves based on analyzed data and data obtained from execution of the evaluation program.

In any of the above or another example, the evaluation program is configured to identify presence of autism or autism linked behaviors that includes presenting an infant with social and non-social stimuli and analyzing collected data representative to the infant's response to the presented social and non-social stimuli.

In any of the above or another example, the evaluation program further comprises collection of motion data with respect to the eyes or gaze of the infant while a caregiver looks or speaks to the infant.

In any of the above or another example, the evaluation program comprises collection of motion data with respect to the eyes or gaze of the infant while a caregiver looks away or ignores the infant.

In any of the above or another example, the collected data includes heart rate, respiration, body temperature, heart rate variability, galvanic skin response, or combination thereof.

In any of the above or another example, the collected data further or alternatively relates to vocalizations, facial expression, head turn, smile, aversion of gaze, join attention, and/or aversion of gaze.

In any of the above or another example, the analysis includes comparing the collected data to expected normal measurements.

In any of the above or another example, the evaluation module integrate the evaluation program with one or more peripherals selected from lights, graphical displays, tactile/haptic devices, speakers, evaluation objects, motor/actuators, or user interfaces to measure voluntary or involuntary responses of the subject to stimuli or conditions. In one example, the peripheral comprises the evaluation object, and wherein the evaluation object is configured to undergo one or more motions within view of an infant. In any of the above or another example, the evaluation object comprises a 3D evaluation object and a motor or actuator is operatively associated with the 3D evaluation object to cause the 3D evaluation object or a graphical display thereof to display a motion. In one example, the 3D evaluation object comprises a toy or a mobile. In a further example, the 3D evaluation object comprises a toy with eyes that include a camera for detecting fixation on eyes. In any of the above or another example, the 3D evaluation object includes reflective surfaces, wherein the 3D evaluation object includes speakers for outputting a voice of a caregiver.

In any of the above or another example, a motion sensor is configured to collect motion data with respect to the infant to track eyes or gaze of the infant during the one or more motions.

In any of the above or another example, the evaluation program further comprises collection of motion data with respect to the eyes or gaze of the infant while a caregiver looks or speaks to the infant during the one or more motions.

In any of the above or another example, the evaluation program further comprises collection of motion data with respect to the eyes or gaze of the infant while a caregiver looks away or ignores the infant during the one or more motions.

In any of the above or another example, the evaluation program is part of an autism identification, object tracking, or eye teaming evaluation.

In any of the above or another example, the evaluation program further includes changing parameters of the evaluation object selected from size, color, rate of motion, or the type of evaluation object.

In any of the above or another example, the evaluation module includes a catalog of evaluation programs to evaluate various developmental milestones, skills, and/or potential medical conditions with respect to the infant.

In any of the above or another example, the evaluation module utilizes data and/or analysis performed by one or more additional modules selected from a motion analysis module, sound analysis module, vital analysis module, environmental analysis module, weight module, sleep state analysis module, or combination thereof.

In any of the above or another example, the analysis of data obtained during the evaluation program includes inputting the data alone or together with additional data related to the infant into an AI scheme to generate a predictive output with respect to the evaluation.

In any of the above or another example, the evaluation module is configured to cause an output of a report that depicts or identifies what data is changing over time, why it is happening, what a caregiver or medical provider may expect to arise in the future with and/or without intervention, tips or tricks to treat or address issues or deficiencies, and/or advice regarding intervention steps, wherein the report further includes raw or analyzed historical data with respect to the infant to be given to a medical care provider.

In a sixth aspect, alternatively or in addition to the any of the first through fifth aspects or any configurations or examples thereof, the system includes a sleep state module configured to identify a sleep state of an infant.

In one example, the sleep state module is configured to analyze motion data, respiration data, heart rate data, blood pressure, sound data, or combination thereof to identify the sleep state.

In the above or another example, the analysis is configured to identify sleeps cycles or sleep patterns.

In any of the above or another aspect, the sleep state module is configured to input the sleep related data or analysis thereof alone or together with additional data related to the infant into an AI scheme to generate a predictive output with respect to sleep cycles or sleep patterns.

In any of the above or another aspect, the sleep state includes an awake state and a asleep state.

In any of the above or another aspect, the asleep state includes non-rapid eye movement (NREM) and rapid eye movement (REM). In one example, the NREM sleep state includes 3 substates N1-N3. N1.

In any of the above or another aspect, the sleep state module utilizes data and/or analysis performed by one or more additional modules selected from a motion analysis module, sound analysis module, vital analysis module, environmental analysis module, weight module, evaluation analysis module, or combination thereof.

In a seventh aspect, alternatively or in addition to the any of the first through sixth aspects or any configurations or examples thereof, the system includes a condition identification module configured to identify medical conditions or events.

In one example, the condition identification module is configured to analyze sensor data together or alone with input data.

In the above or another example, the condition identification module is configured to utilized analyses generated by one or more of additional modules selected from a motion analysis module, sound analysis module, vital analysis module, environmental analysis module, weight module, sleep state module, evaluation analysis module, or combination thereof.

In any of the above or another example, the condition identification module is configured to analyze data collected by a plurality of sensors selected from a sound sensor, motion sensor, optical sensor, vibration sensor, or biological sensor.

In any of the above or another example, the condition identification module is configured to detect medical and/or developmental issues selected from one or more of fever, fever precursors, abnormal breathing, type of abnormal breathing, cough, type of cough, vision abnormalities such as strabismus, seizures, seizure precursors, temperament of infant, hyperactivity, autism, or developmental delay.

In any of the above or another example, the condition identification module is configured to execute a hearing evaluation program that includes identifying hearing or auditory response conditions. In one example, the hearing evaluation program includes outputting various sound frequencies and volumes to speakers.

In any of the above or another example, the condition identification module is configured to utilize breathing and/or respiration analysis of data collected by one or more respiration sensors to identify or predict a respiratory condition selected from cough, croup, or asthma.

In one example, the condition identification module utilizes a modeling engine to identify early on-set of an illness selected from respiratory infections, cold, flu, respiratory syncytial virus, or Roseola.

In any of the above or another example, the data analyzed includes body temperature, blood oxygen, heart rate sensor, electrodermal data, or combination thereof.

In any of the above or another example, the data analyzed further includes sound data selected from breathing, vocalizations, or combination thereof.

In any of the above or another example, the data analyzed includes optical or infrared video data of the infant.

In a first configuration of the seventh aspect, which may be in the alternative or further to any of the above examples, the condition identification module is configured to identify a neurological conditions. In one example, the identification includes analysis of collected data including motion data, sound data, or both over time to identify patterns therein. In a further example, the motion data is selected from head, facial, and/or eye movements, and wherein the sound data includes infant vocalizations while alone or during interactions with caregivers and/or objects for early detection of neurological conditions. In any of the above or another example, identification includes analysis of motion data, sound data, or both of the infant.

In a second configuration of the seventh aspect, which may be in the alternative or further to the first configuration or any of the above examples, the motion data is selected from head, facial, and/or eye movements, and wherein the sound data includes infant vocalizations while alone or during interactions with caregivers and/or objects for early detection of neurological conditions. In one example, the motion data includes infrared video data and that is analyzed alone or together with collected sound data and/or situational data. In a further or another example, the collected data may be analyzed to identify head turn, smile, aversion of gaze, join attention, aversion of gaze, interest in objects over people, auditory ques, and/or dysphonic sounds for early identification of neurological conditions. In any of the above or another example, the collected data is analyzed to compare and/or identify lack of activities, facial expressions, and/or other ques. In one example, the comparison includes comparison of observed eye movement to an expected eye movement model. In one example, the expected eye movement model tracks a caregiver over an object. In the above or another example, the analysis includes measuring duration of fixation on an object to identify if the duration taken for the infant to become bored with the object is within a predefined normal range. In any of the above or another example, the collected data comprises motion data that is analyzed for habitualization behavior indicative of autism.

In any of the above or another example, wherein the collected data include vital data collected by biological sensors such as body temperature, respiration, galvanic skin response, heart rate, heart rate variability, and/or other collected data relating to physiological state or response of an infant to stimuli for early detection of neurological conditions.

In any of the above or another example, the condition identification module is configured to cause an output of a report that depicts or identifies what data is changing over time, why it is happening, what a caregiver or medical provider may expect to arise in the future with and/or without intervention, tips or tricks to treat or address issues or deficiencies, and/or advice regarding intervention steps.

In any of the above or another example, the report further includes raw or analyzed historical data with respect to the infant to be given to a medical care provider.

In an eighth aspect, alternatively or in addition to the any of the first through seventh aspects or any configurations or examples thereof, the system includes a modeling engine configured to apply machine learning (ML) and/or artificial intelligence (AI) processing to infant data.

In one example, the modeling engine is configured to generate predictive and/or AI/ML models to receive raw and/or analyzed infant data collected by the plurality of sensors alone or together with input data.

In the above or another example, the modeling engine is configured to generate predictive outputs.

In any of the above or another example, the modeling engine is configured to generate response instructions.

In any of the above or another example, the response instructions include generation of a report using a report module, collection of more data with the plurality of sensors, or further analysis of data identified in the response instructions or to be collected by the plurality of sensors.

In any of the above or another example, the infant analysis system includes a controller configured to receive the response instructions, and wherein the controller is configured to initiate an operation of one or more of the peripherals.

In any of the above or another example, the operation comprises an operation selected from initiation, termination, or modification of a motion of a sleep platform that supports the infant; modification of a temperature, feeding schedule, feeding volume, lighting, or other environmental condition.

In any of the above or another example, the modeling engine is configured to transmits raw and/or collected sensor or input data to a storage medium for future analysis and/or use in connection with updating predictive and/or AL/ML models with current and/or the historical infant data.

In any of the above or another example, the modeling engine is pre-programed with one or more predictive models that may be modified using specific data collected by the plurality of sensors and/or input into the infant analysis system.

In any of the above or another example, the modeling engine is configured to receive raw and/or analyzed input and/or collected data from a population of analysis units to develop new and/or improve current models.

In any of the above or another example, the modeling engine is configured to transmit raw and/or analyzed input and/or collected data to a central resource to develop new and/or improve current models.

In any of the above or another example, modeling engine is configured to transmit raw and/or analyzed input and/or collected data to a central resource for predictive processing and receive a predictive output from the central resource with respect to the transmitted data.

In any of the above or another example, the modeling engine is further configured to receive output response instructions from the central resource.

In one example, the response instructions include generation of a report using a report module, collection of more data with the plurality of sensors, or further analysis of data identified in the response instructions or to be collected by the plurality of sensors.

In the above or another example, the report depicts or identifies what data is changing over time, why it is happening, what a caregiver may expect to arise in the future with and/or without intervention, tips or tricks to treat or address issues or deficiencies, and/or advice regarding intervention steps.

In any of the above or another example, the infant analysis system includes a controller configured to receive the response instructions, and wherein the controller is configured to initiate an operation of one or more of the peripherals.

In any of the above or another example, the operation comprises an operation selected from initiation, termination, or modification of a motion of a sleep platform that supports the infant; modification of a temperature, feeding schedule, feeding volume, lighting, or other environmental condition.

In any of the above or another example, the predictive outputs relate to a current or future predictive medical condition or developmental condition.

In any of the above or another example, the medical or developmental condition is selected from one or more of fever, fever precursors, abnormal breathing, type of abnormal breathing, cough, type of cough, vision abnormalities such as strabismus, seizures, seizure precursors, auditory response conditions, SIDS, temperament of infant, hyperactivity, autism, or developmental delay.

In an ninth aspect, alternatively or in addition to the any of the first through eight aspects or any configurations or examples thereof, the system includes a user interface configured to receive input data from a user related to the infant.

In one example, the input data is selected from date of birth, gestation age at birth, medical conditions, family history, due date, name or an identifier infant, sex, weight, feeding information, weight at birth, gestation age, length at birth, length at different points in time, circumference of waist, circumference of a limb, circumference of head at birth, current circumference of head current, circumference of waist, frequency of urination, travel, immunizations, illness, heart rate, respiratory rate, or blood oxygenation.

In the above or another example, the user interface is integrated with a sleep device and/or remote. In one example, the user interface comprises a mobile app.

BRIEF DESCRIPTION OF THE DRAWINGS

For a complete understanding of the present disclosure and its features and advantages, reference is now made to the following description, taken in conjunction with the accompanying drawings, in which:

FIG. 1C illustrates various sensors that may be utilized with an analysis unit of an infant analysis system according to various embodiments described herein;

DETAILED DESCRIPTION

Figure 1A:
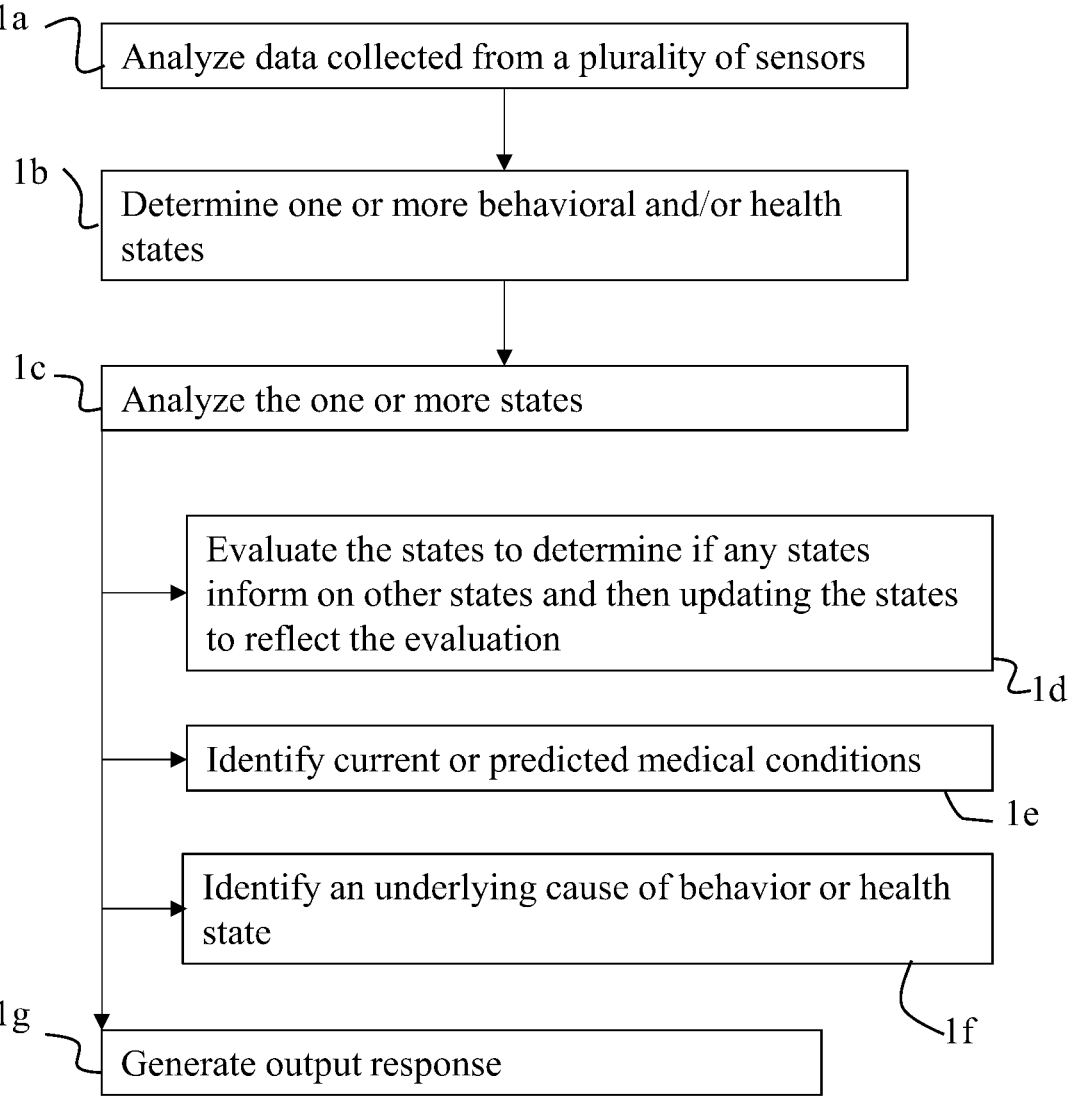
FIG. 1A illustrates an operation of an infant analysis system according to various embodiments described herein.

An infant analysis system may include an analysis unit configured to analyze data collected from a plurality of sensors that measure various parameters with respect to an infant and/or an environment in which the infant is present.

In various embodiments, the analysis may include evaluations of behavioral states, developmental states, and/or medical conditions (e.g., health state). For example, the analysis may include identification of a behavioral state of the infant. Behavioral states may be states or conditions with respect to the infant, such as a cry state (e.g., bored, hungry, unwell, tired, or content), sleep state (e.g., awake, awakening, asleep, sleep stage, unlikely to return to sleep, tired, nap, long sleep), or hunger state (e.g., satiated, preferred state for feeding, hungry). In some embodiments, a cry state may be used to indicate or inform another state such as a health state, hunger state, or sleep state.

In one example, the analysis includes a cry analysis that identifies nuances in collected and/or calculated data to determine a cry state of the infant. As noted above, the cry state may be a behavior state or may be a component of a behavior state. Identification of a cry state may be used to better understand and/or respond to an infant behavior, condition, or need. Cry analysis data may include analysis of sound data collected during infant cries. In some examples, cry analysis may also include analysis of data collected related to one or more of infant motion, vitals, or weight. For instance, weight of an infant may be analyzed and compared to previous and/or expected infant weight measurements to determine if the infant has a weight indicative of having recently eaten and is unlikely to be crying due to hunger or if the infant has lower weight than previously measured or expected indicating the infant may have an empty stomach and the crying may be associated with hunger. The cry analysis may, for example, include comparisons of a set of current collected data to one or more sets or models of data previously collected with respect to the infant. Additionally or alternatively, the cry analysis may include comparison of the set of current data collected with one or more sets of data previously collected with respect to a plurality of infants or models derived therefrom.

In an above or another example, analyses performed by the infant analysis system may include a weight analysis of the infant to determine if the infant is hungry or satiated, which may be used to determine or inform a cry state, hunger state, or other behavioral state. For example, if an infant is hungry, it may be difficult to soothe the infant. Weight data collected over time may be compared to a current weight of an infant to identify if the infant is hungry. If the infant is identified as being hungry, this information may assist in informing a cry analysis or vice versa.

The system may utilize other collected and/or calculated data to identify and/or evaluate developmental conditions such as autism, illnesses, or various medical conditions.

The various analysis processes described herein may apply analytics to the collected data. The analysis may apply machine learning, such as artificial intelligence.

Figure 1B:
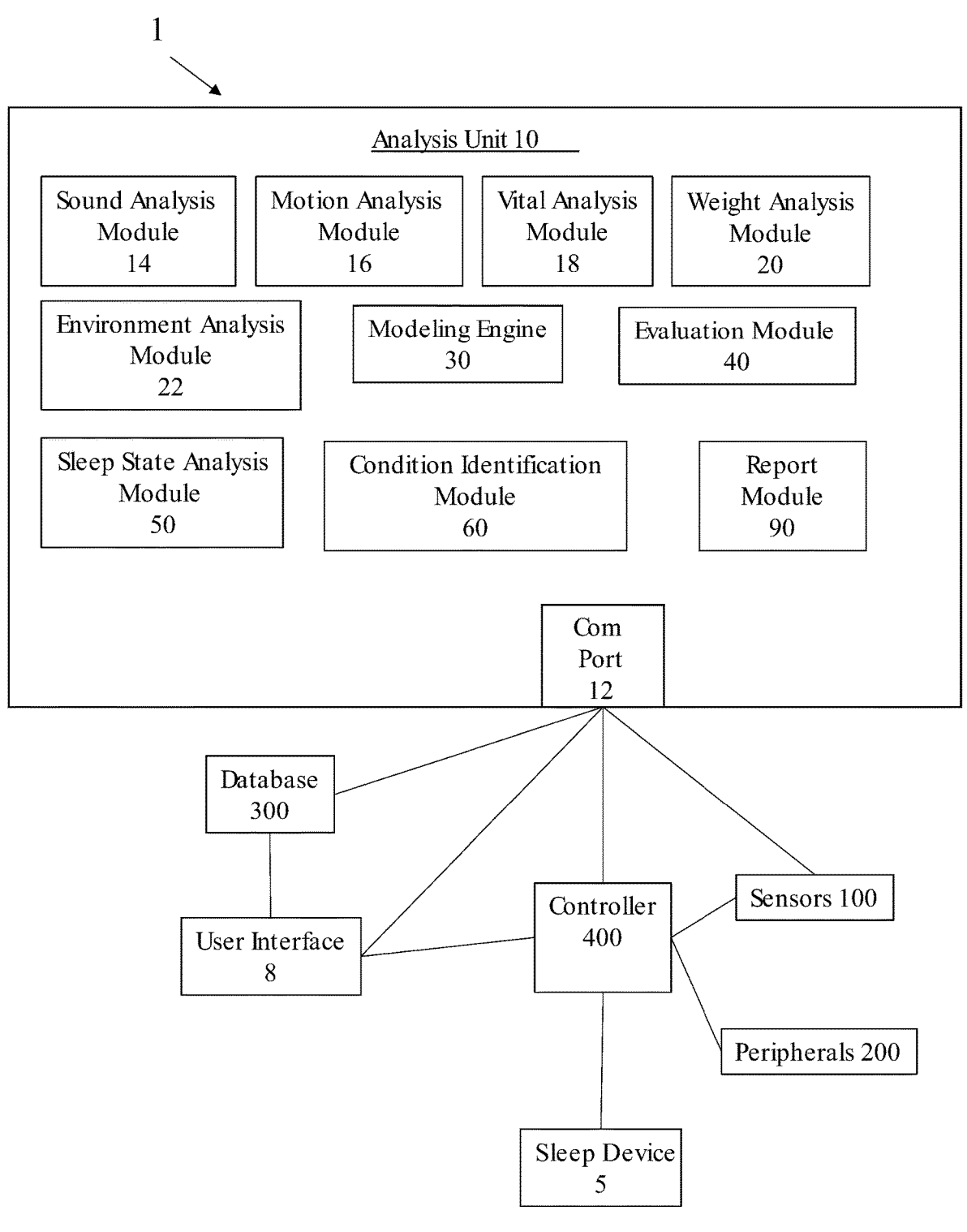
FIG. 1B illustrates an infant analysis system 1 including an analysis unit according to various embodiments described herein.

FIGS. 1A-1D illustrate various features of an infant analysis system 1 according to various embodiments wherein like features are identified by like numbers. It is to be appreciated that the analysis system may include additional features as well as fewer features, including any combination of those shown and/or described herein. For example, while FIG. 1B illustrates the infant analysis system 1 as including a sleep device 5, user interface 8, analysis unit 10, sensors 100, peripherals 200, database 300, and controller 400, in various embodiments, the infant analysis system 1 may comprise or consist of analysis unit 10. In one embodiment, the infant analysis system 1 may comprise or consist of analysis unit 10 and sensors 100 or analysis unit 10, sensors 100, peripherals 200, and controller 400.

With reference to FIG. 1B an infant analysis system 1 may include an analysis unit 10 configured to analyze data related to an infant, which may include an environment in which the infant is present. The data may include data collected by sensors 100 and/or input into the system 1, e.g., via a user interface 8. The analysis unit 10 may also utilize other data such as data calculated from collected or input data associated with the infant or a population of infants, which may include historical and/or predictive models. The analysis unit 10 may include any combination of modules, submodules, or engines configured to execute the operations of the analysis unit 10. While FIG. 1B illustrates various modules and engines of an exemplary analysis unit 10, the analysis unit 10 may include fewer, additional, or any combination of the illustrated modules, submodules, and/or engines.

FIG. 1A illustrates an operation of an analysis system 1 according to various embodiments. The analysis system 1 may be configured to analyze data collected from a plurality of sensors 1a. The analysis may be used to determine one or more behavioral and/or health states 1b. They analysis system 1 may further analyze the one or more states 1c, which may include evaluating the states to determine if any of the states inform on other states and then updating the states to reflect the evaluation 1d; identify current or predicted medical conditions 1e; or identify an underlying cause of behavior or health state 1f. From the analysis, the analysis system 1 may generate an output response 1g.

In various embodiments, the infant analysis system 1 may include or be associated with a sleep device 5 such as a bassinet or crib. In some embodiments, the infant analysis system 1 may be integrated or integrable with such a sleep device 5. In one example, the infant analysis system 1 is integrated or integrable with a sleep device 5 similar to that described in U.S. patent application Ser. No. 14/448,679, filed Apr. 31, 2014, or U.S. patent application Ser. No. 15/055,077, filed Feb. 26, 2016, both of which are incorporated herein. The present description references utilization of the infant analysis system 1 to analyze infant behaviors and/or conditions. Infants typically include children up to two years old. However, it is to be appreciated that the infant analysis system 1 may be used in a similar manner for analysis of older humans.

The infant analysis system 1 may include or be in data communication with plurality of sensors 100. The sensors 100 may be configured to collect data associated with an infant, which may include environmental data with respect to an environment surrounding the infant.

The analysis unit 10 may include a communication port 12, e.g., receiver or transceiver, configured to receive collected data from sensors 100. In various embodiments, the communication port 12 receives data collected by sensors 100 via wired and/or wireless communications. In some embodiments, the analysis unit 10 may be configured to communicate and/or control sensors 100 to initiate data collection, define timing of data collection, and/or specify a manner of data collection.

With further reference to FIG. 1C, illustrating exemplary sensors 100, sensors 100 may include one or more sound sensors 110, biological sensors 120, environmental sensors 130, motion sensors 140, or combinations thereof. It is to be appreciated that the infant analysis system 1 may include any combination of the listed sensors 100, and sensors 100 may fall into multiple of such functional categories. For example, biological sensors 120 or environmental sensors 130 may include motion sensors 140 and/or sound sensors 110 configured to detect biological or environmental motion or sound. Sound sensors 110 or motion sensors 140 configured for collecting biological data, which may include vital data and/or physiological data, may be the same or different sensors than sound sensors 110 or motion sensors 140 configured to collect environmental data. For example, video camera 140a may be utilized for collecting biological/physiological data, and infrared sensor 140b may be utilized for collecting temperature data. In various embodiments, the analysis unit 10 may be configured to stabilize collected video data. In one embodiment, the analysis unit 10 is configured to apply stabilization processing to video data utilizing global movement image stabilization techniques disclosed in U.S. patent application Ser. No. 17/136,228, filed Dec. 29, 2020, the contents of which are hereby incorporated herein by reference.

Sound sensors 110 may be configured to collect sound data associated with an infant and/or surrounding environment. Example sound sensors may comprise or consist of one or more microphones 110a, such an unidirectional microphone 110b or omnidirectional microphone 110c.

Biological sensors 120 may be configured to collect biological data associated with an infant. In various embodiments, biological data may include vital data and/or physiological data. Example, biological sensors 120 may comprise or consist of one or more sensors selected from a blood oxygenation sensor 120a, heart rate sensor 120b, body temperature sensor 120c, respiration sensor 120d to detect breathing rate or depth, weight sensor 120e, and/or other sensors for detection of other biological parameters such as galvanic skin response or electrodermal activity sensors 120f. In one example, biological sensors 120 include sensors configured to collect electrocardiogram data.

Blood oxygenation sensors 120a may be configured to collect blood oxygenation data. For example, blood oxygenation sensors 120a may measure blood oxygen or oxygen saturation by detecting absorption of infrared light and may include a pulse oximeter sensor. Heart rate sensors 120b may utilize any suitable methodologies to collect heart rate data, such as optical, sound, vibration, motion, and/or pressure.

Respiration sensors 120d may be configured to collect respiration data associated with an infant. Respiration sensors 120d may include one or more motion sensors 140 and/or sound sensors 110 configured to detect movement, vibrations, and/or sound associated with breathing. Respiration sensors 120d may include, for example, a video camera 140a and/or other optical sensor, such as visible or non-visible, e.g., infrared, spectrum video, configured to detect movement associated with breathing. In one embodiment, respiration sensor 120d may include a breathing sensor as described in U.S. patent application Ser. No.

16/905,424, filed Jun. 18, 2020, the contents of which are hereby incorporated by reference herein.

Weight sensors 120*e* may be configured to collect weight data associated with an infant. Example weight sensors 120*e* may include piezo-electric sensors and/or pressure gages. In one embodiment, weight sensor 120*e* may include a weight sensor as described in U.S. patent application Ser. No. 17/006,223, filed Aug. 28, 2020, the contents of which are hereby incorporated by reference herein.

Environmental sensors 130 may include one or more environmental sensors 130 selected from air quality sensors 130*a* for detecting air quality, environmental temperature sensors 130*b* for measuring ambient temperature and/or temperature of bedding, optical/light sensors 130*c* for detecting ambient light, sound sensors 110 for detecting environmental sounds, motion sensors 140 for detecting motion of objects around the infant. In some embodiments, air quality sensors 130*a* may be configured to detect one or more of carbon dioxide levels, dust, temperature, humidity, ozone, or barometric pressure. In some embodiments, weight sensors 120*e* may be used to identify potentially hazardous events of conditions with respect to the environment. For example, sudden increases in weight may indicate an object has fallen onto a platform of a sleep device 5, such as a crib or bassinet, supporting the infant.

Motion sensors 140 may be configured to detect motion with respect to the infant, environment surrounding the infant, or both. Example motion sensors 140 may include one or more sensors selected from optical sensors such as video cameras 140*a* and/or infrared sensors 140*b*, accelerometers 140*c*, vibration sensors 140*d*, piezo electric sensors 140*e*, and/or pressure gages 140*f*.

In various embodiments, the analysis unit 10 may analyze sensor data together with other collected data such as user input data. Input data may include information related to the infant such as one or more of birth weight, gestation period, infant medical history, sex, family medical history, developmental stage or indicators, head circumference, food intake, breast fed, formula fed, mixture of breast and formula fed, type of formula, feeding duration, feeding schedule, or bowel movement times and/or descriptions.

Input data may also include information entered by a user that the analysis unit 10 may use to generate recommendations for output to provide the user. For example, a user may input a desired sleep schedule that the analysis unit 10 may use to develop feeding recommendations regarding time and duration/amount of feedings to encourage the desired sleep schedule.

As introduced above, the analysis unit 10 may be configured to analyze data associated with the infant, which may include biological, environmental, motion, sound, or combination thereof. The analysis unit 10 may be local or remote with respect to one or more of the various sensors 100 and/or a sleep device 5. For example, the analysis unit 10 may be attached to or located on or proximate to one or more sensors 100 and/or sleep device 5 in which the sensors 100 are configured to collect data associated with an infant in the sleep device 5 or surrounding environment. In another example, the analysis unit 10 is remote with respect to one or more of the various sensors 100 and/or sleep device 5. In such configurations, sensors 100 may communicate with the analysis unit 10 via the communication port 12 directly or indirectly, e.g., one or more intermediate communication devices or protocols such as RF, near field, cellular, Wi-Fi, and/or Bluetooth receivers, transmitters, or transceivers; smart home hubs; modems, Wi-Fi enabled devices; or wired networks and/or wireless networks.

In one embodiment, the analysis unit 10 is distributed such that one or more processing and/or analysis functions are executed locally and one or more processing and/or analysis functions are executed remotely. For example, the analysis unit 10 may receive and analyze sensor data and/or input data locally and/or transmit all or a portion of the raw and/or analyzed data to a remote processor or a central or back-end resource for archiving, further analysis, use in data modeling relating to the infant or population trends and/or comparative analyses relating to a plurality of infants, or in other operations.

In one embodiment, raw and/or analyzed data can be transmitted to a back-end system for further analysis and historical storage. In such analyses, population trends, individual historical trends, or other trends may be identified. In a further or another example, analyses may include comparative analysis of individual infants versus population. The analysis unit 10 may transmit raw and/or analyzed data, e.g., collected or input data to a central resource, which may comprise a back-end system, for input or analysis together with inputted, raw collected data, and/or analyzed data obtained by other infant analysis systems 1. In one example, the central resource and the collective infant analysis systems 1 comprise a network wherein all or a portion of the data collected and/or analyzed may be shared. The data collected and/or analyzed from the collective of infant analysis systems 1 may be used to generate new data models or update current data models, which may be subsequently utilized to improve analysis operations of the analysis unit 10, which may include the modeling engine 30. It is to be understood that one or more of the various sensors 100 may be configured to directly and/or indirectly transmit collected data to a central or remote resource instead of or in addition to transmitting the collected data to the analysis unit 10.

In some embodiments, the analysis unit 10 may receive data other than data collected by sensors 100 and/or data input by a user. For example, the analysis unit 10, which may include modeling engine 30, may receive new or updated data models, machine learning training data, data analysis from remote resources, and/or analysis tools or protocols.

In various embodiments, the analysis unit 10 includes a modeling engine 30 configured to apply machine learning (ML) and/or artificial intelligence (AI) processing to the data to generate outputs described herein. The modeling engine 30 may apply raw and/or analyzed data collected and/or input into the infant analysis system 1 to generate predictive outputs. The modeling engine 30 may be configured to develop predictive models from the data collected and/or input into the infant analysis system 1. The modeling engine 30 may be pre-programed with one or more predictive models that may be modified using specific data collected by or input into the infant analysis system 1.

In one embodiment, the modeling engine 30 includes or integrates data input and/or collected from other analysis units 10 of other sleep systems 1 or sources to develop and/or improve predictive models for use in generating predictive outputs. For example, multiple analysis units 10 associated with multiple infant analysis systems 1 and/or sleep devices 5 may provide data to the analysis unit 10 for use by the modeling engine 30 to develop and/or modify predictive models. In a further or another example, multiple analysis units 10 associated with multiple infant analysis systems 1 and/or sleep devices 5 may transmit data to a central resource. The central resource may transmit all or a portion of the data to the analysis unit 10 for use by the modeling engine 30 to develop and/or modify predictive models. In one example, the central resource analyzes the data and provides predictive models for the modeling engine 30. The modeling engine 30 may utilized the models provided by the central resource or may modify the models utilizing data collected and/or analyzed by the specific infant analysis system 1. Thus, in some embodiments, the analysis unit 10 may utilize raw and/or analyzed data from other infant analysis systems 1 to improve data analysis.

In some embodiments, the analysis unit 10 may transmit raw and/or analyzed collected data, e.g., sound data, motion data, wake/sleep or sleep cycle data, weight data, vitals data, environmental data, feeding data, or combination thereof, and/or user input data, to a data storage medium, identified as database 300. In one embodiment, all or a portion of the analysis unit 10 and/or database 300 comprises one or more servers and/or cloud networks configured to archive and/or analyze the data. Portions of the raw or analyzed data may be utilized to build predictive models and/or apply AI or ML to make predictions based on the data. For example, the modeling engine 30 may access the database 300 to store or obtain data for using in predictive modeling operations.

The infant analysis system 1 may include or be configured to be in data communication with one or more peripheral devices 200. For example, the analysis unit 10 may utilize the communication port 12 to transmit data or operation instructions directly or indirectly to peripheral devices 200 for output by the same. In one example, the analysis unit 10 may provide analysis data and/or operation instructions to peripheral devices 200 via a controller 400, wherein the controller 400 is configured to control the operations of one or more of the peripheral devices 200 and/or sensors 100. The controller 400 may similarly be configured to identify suitable outputs in response to analysis data transmitted by and/or analyzed by the analysis unit 10. Thus, the analysis unit 10 may provide analysis data to the controller 400 and the controller may determine corresponding outputs to instruct peripheral devices 200 to output. However, for brevity, herein the analysis unit 10 is generally described as providing operation instructions to peripheral devices 200 and sensors 100, when applicable, herein, but it is to be appreciated that such instructions may be indirect via the controller 400 which may generate instructions based on analyzed data from the analysis unit 10 or cause peripheral devices to generate outputs based on instructions provided by the analysis unit 10.

Figure 1D:
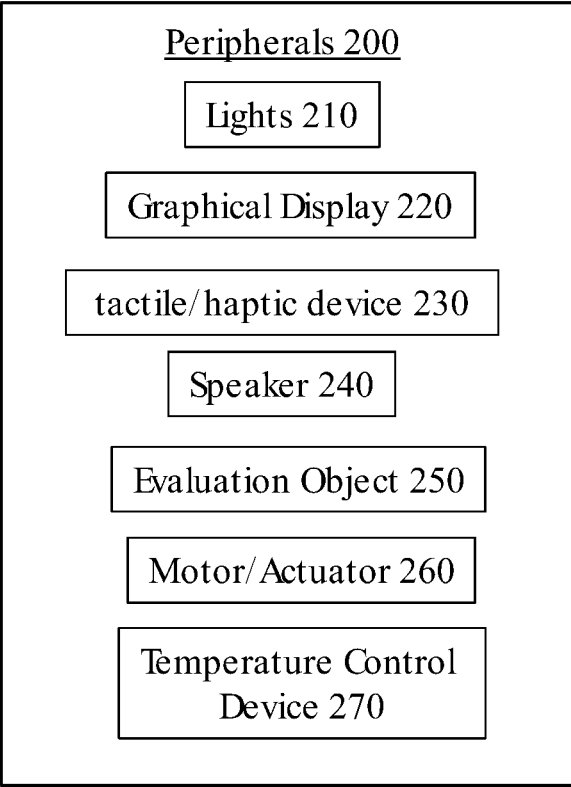
FIG. 1D illustrates various peripheral devices that may be utilized with an analysis unit of an infant analysis system according to various embodiments described herein.

Peripheral devices 200 may be configured to produce outputs such as stimuluses. With further reference to FIG. 1D, illustrating exemplary peripheral devices 200, peripheral devices 200 may include lights 210 for outputting light, electronic graphical displays 220 for producing displays on a display screen, tactile/haptic devices 230 such as touch screens, buttons, and/or controllers, speakers 240 for outputting sound, evaluation object 250 for utilization in evaluating an infant, actuators 260 for moving objects such as a platform supporting the infant, a mobile, toy, or evaluation object 250, and/or temperature control devices 270 (e.g., fans, heaters, air coolers) for modifying environmental temperature proximate to an infant. Further to the above, peripheral devices 200 may include or be in operable communication with a user interface 8 for receiving actions, communications, instructions, and/or data from a user. As explained in more detail below, the analysis unit 10 may include an evaluation module 40 wherein one or more operations of the evaluation module 40 includes initiating or causing a peripheral device 200 to generate an output or stimulus and utilizing the peripheral device 200 and/or sensors 100 to collect response or reaction data with respect to the infant. In some embodiments, peripheral devices 200 include or integrate one or more sensors 100 described herein. For example, an evaluation object 250 may include a toy including a camera configured to track eye movements or gaze of an infant. The infant analysis system 1 may include additional, fewer, or any combination of peripheral devices 200 illustrated in FIG. 1D.

Figure 2:
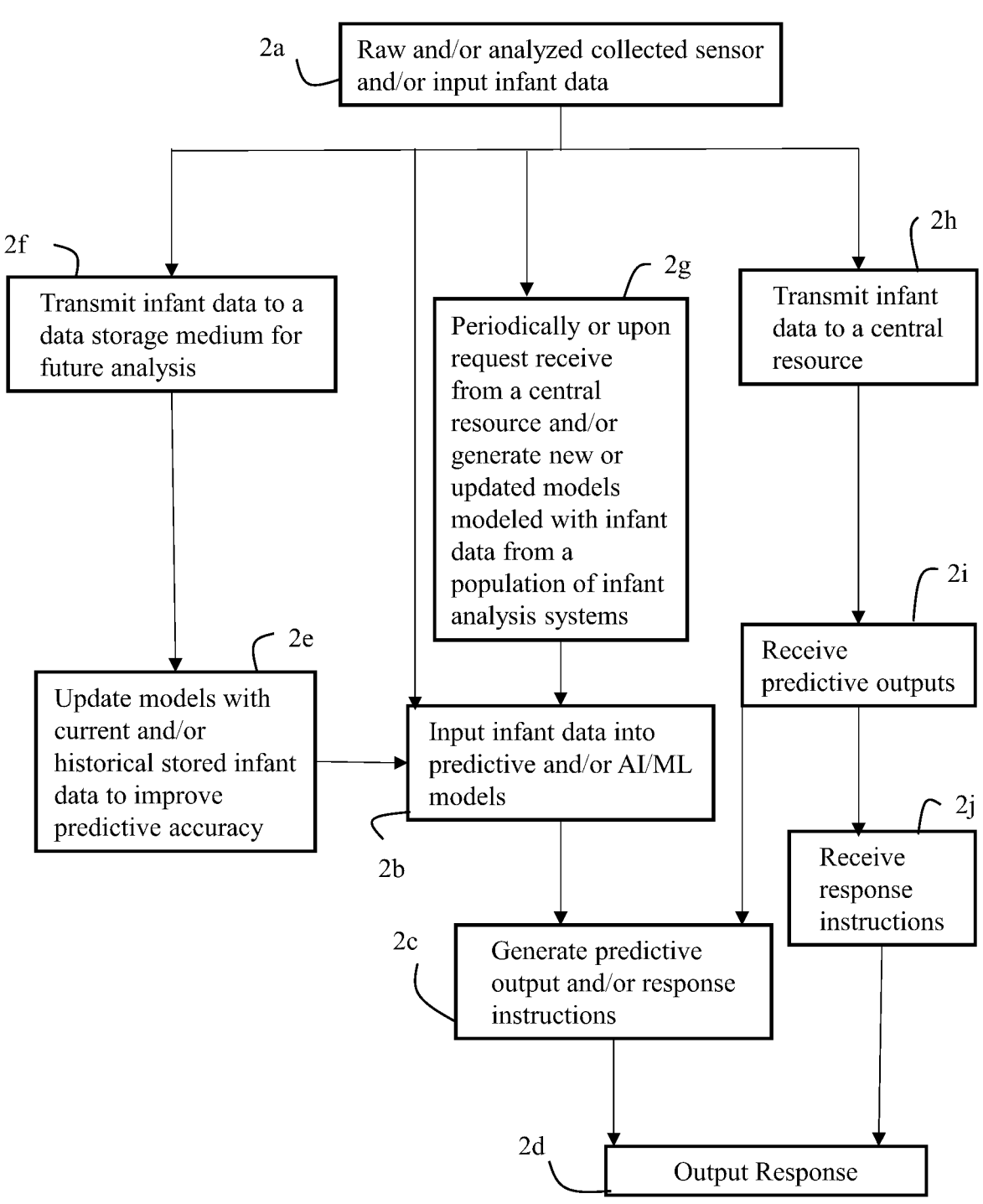
FIG. 2 illustrates operations of a modeling engine according to various embodiments described herein.

FIG. 2 illustrates operations of a modeling engine according to various embodiments described herein. The modeling engine configured to apply machine learning (ML) and/or artificial intelligence (AI) processing to infant data. The modeling engine may utilize raw and/or analyzed collected sensor and/or input infant data 2a. In one example, the modeling engine is configured to input the infant data into predictive and/or AI/ML models 2b and generate predictive outputs and/or response instructions 2c. In one example, the modeling engine is configured to transmit raw and/or collected sensor or input data to a storage medium for future analysis 2f and/or use in connection with updating models with current and/or the historical infant data to improve predictive accuracy 2e. In one example, the modeling engine is configured to receive raw and/or analyzed input and/or collected data from a population of analysis units to develop new and/or improve current models 2g. In one example, the modeling engine is configured to transmit raw and/or analyzed input and/or collected data to a central resource 2h for predictive processing and receive a predictive output 2i from the central resource with respect to the transmitted data. The modeling engine may be further configured to receive output response instructions 2j from the central resource. The controller may be configured to output a response 2d based on the response instructions.

As introduced above, and with continued reference to FIGS. 1A-1D, the analysis unit 10 may include one or more modules configured to perform the operations described herein with respect to the analysis unit 10. In various embodiments, the modules may include but are not limited to, one or more of a sound analysis module 14, motion analysis module 16, vital analysis module 18, weight analysis module 20, environment analysis module 22, or evaluation module 40. One or more of the above modules may be configured to apply AI or other ML, e.g., in conjunction with modeling engine 30, utilizing one or more data types or portions thereof as inputs into one or more predictive models.

A sound analysis module 14 of the analysis unit 10 may be configured to analyze collected data related to sounds produced by an infant being monitored. For example, the sound analysis module 14 may be configured to analyze collected sound data to perform voice analysis, cry analysis, or otherwise analyze collected sound data. In some embodiments, the sound analysis module 14 may be configured to filter collected sound data to determine if the sound is a cry and/or if the sound originated from the infant being monitored, e.g., via directional filtering of the sound for location of origination. The sound analysis module 14 may be configured to analyze various sound parameters of collected sound data such as tone, amplitude, wavelength, frequency/pitch, or duration.

The sound analysis module 14 may apply analytics to raw, processed, and/or analyzed sound data. The analytics may include identifying sound patterns alone or in relation to non-sound data or patterns therein. In some embodiments, the sound analysis module 14 may apply AI or other ML scheme, e.g., via the modeling engine 30, utilizing collected sound data or a portion thereof alone or in combination with one or more sets of collected non-sound data and/or analyses thereof. The sound analysis module 14 may utilize data and/or analysis performed by one or more additional modules such as the motion analysis module 14, vital analysis module 18, weight analysis module 20, environmental analysis module 22, evaluation module 40, sleep state analysis module 50, or combination thereof. Additionally or alternatively, the sound analysis module 14 may associate with the evaluation module 40 and/or condition identification module 60 to provide sound data or analyses thereof according to an evaluation program and/or for identification of a condition.

A motion analysis module 16 of the analysis unit 10 may be configured to analyze collected data related movement of an infant. The movement may correspond to leg movement, eye movement, arm movement, body movement, head movement, or other movement such as movement of feet, toes, mouth, hands, or fingers. The movements may be analyzed alone or in combination and may include analysis of rate, duration, pattern, and/or distance of movement.

The motion analysis module 16 may apply analytics to raw, processed, and/or analyzed motion data. The analytics may include identifying motion patterns alone or in relation to non-motion data or patterns therein. In some embodiments, the motion analysis module 16 may apply artificial intelligence or other machine learning, e.g., via the modeling engine 30, utilizing collected motion data or a portion thereof alone or in combination with one or more sets of collected non-motion data and/or analyses thereof. The motion analysis module 16 may utilize data and/or analysis performed by one or more additional modules such as the sound analysis module 14, vital analysis module 18, weight analysis module 20, environmental analysis module 22, evaluation module 40, sleep state analysis module 50, or combination thereof. Additionally or alternatively, the motion analysis module 16 may associate with the evaluation module 40 and/or condition identification module 60 to provide motion data or analyses thereof according to an evaluation program and/or for identification of a condition.

A vital analysis module 18 may be configured to analyze collected data related to body temperature, pulse rate, respiration rate, and/or blood pressure. The vital analysis module 18 may apply analytics to the raw, processed, and/or analyzed vital data. The analytics may include identifying vital patterns alone or in relation to non-vital data or patterns therein. In some embodiments, the vital analysis module 18 may apply artificial intelligence or other machine learning, e.g., via the modeling engine 30, utilizing the vital data or a portion thereof alone or in combination with one or more sets of collected non-vital data and/or analyses thereof.

The vital analysis module 18 may be configured to analyze collected data related to other respiration parameters. In various embodiments, respiration sensors may include breath detection sensors, such as those described in U.S. patent application Ser. No. 16/905,424, filed Jun. 18, 2020, the contents of which are hereby incorporated by reference herein. In one example, respiration data collected by one or more motion sensors 140, e.g., vibration, optical, and/or sound sensors, may be compared to provide confirmation and/or additional data with respect to respiration. Detection of breathing and breathing parameters such as breathing rate, depth, intervals, and/or patterns thereof may be collected and analyzed. The vital analysis module 16 may utilize data and/or analysis performed by one or more additional modules such as the sound analysis module 14, motion analysis module 16, weight analysis module 20, environmental analysis module 22, evaluation module 40, sleep state analysis module 50, or combination thereof. As introduced above, the vital analysis module 18 may associate with the modeling engine 30 to apply analytics to raw collected and/or analyzed vital data together or separate from other types of data collected by other sensors and/or data analyzed by other modules. Additionally or alternatively, the vital analysis module 18 may associate with the evaluation module 40 and/or condition identification module 60 to provide vital data or analyses thereof according to an evaluation program and/or for identification of a condition.

A weight analysis module 20 of the analysis unit 10 may be configured to analyze collected data related to weight of an infant. Weight may be input by a user, e.g., via a user interface, or collected by a weight sensor 120e. In one example, a weight sensor 120e is integrated with a sleep platform upon which the infant is to be positioned within the sleep device 5. The weight analysis module 20 may be configured to collect weight data for various analysis applications. For example, weight data may be collected for caregivers to help track weight changes over time. In some embodiments, the weight data may be analyzed to determine a feeding state. For example, weight data may be compared to previously collected weight data to determine if the infant is underfed, overfed, or properly fed and/or satiated. The analysis may consider other data collected such as sleep duration, sleep quality, or behavior state associated with previous weight measurements or may compare the weight data to a weight pattern, general or personalized weight profile, or threshold values. In an above or another example, weight data may be analyzed to better understand feeding patterns. For instance, infants may spend a majority of their time in a sleep device 5. Monitoring weight throughout the day may provide insight into feeding patterns and effects of such feeding. For example, feeding patterns may be correlated with sleep patterns for advising caregivers regarding feeding times and amounts. Monitoring weight may be used as a health indicator and/or for early diagnosis of health issues, e.g., when rapid weight loss is observed. Weight may also be monitored as an indicator of motion. For example, weight sensors may be used to detect motion and wiggling of an infant in a sleep device 5. Utilizing signal processing and/or other ancillary information, the weight analysis module 20 may be utilized to determine if the infant is in distress. This may provide critical information to have to predict or identify instances of sudden infant death syndrome (SIDS). In an above or another example, using weight sensors 120e as an indicator of motion may be used to assist in identification of restless sleeping patterns and/or as an indicator of other conditions.

As introduced above, the weight analysis module 20 may associate with the modeling engine 30 to apply analytics and or AI/ML to the raw and/or analyzed data together or separate from data collected from other sensors 100 and/or data analyzed by other modules. For example, the weight analysis module 20 may utilize data and/or analysis of one or more additional modules such as the sound analysis module 14, motion analysis module 16, vital analysis module 18, evaluation module 40, sleep state analysis module 50, or combination thereof. Additionally or alternatively, the weight analysis module 20 may associate with the evaluation module 40 and/or condition identification module 60 to provide weight data or analyses thereof according to an evaluation program or for identification of a condition.

In one embodiment, in addition or alternative to the above, the weight analysis module 20 may be configured to analyze collected data as described with respect to the analysis module in U.S. patent application Ser. No. 17/006,223, filed Aug. 28, 2020, the contents of which are hereby incorporated by reference herein.

The environment analysis module 22 may be configured to analyze collected environmental data related to one or more of ambient or non-infant sounds, motion within a surrounding environment, lighting, air quality, air movement, temperature, or other environmental state.

The environment analysis module 22 may apply analytics to the raw, processed, and/or analyzed environmental data. The analytics may include identifying environment patterns alone or in relation to non-environment data or patterns therein. In some embodiments, the environment analysis module 22 may apply AI or other ML, e.g., via the modeling engine 30, utilizing the environment data, or a portion thereof, alone or in combination with one or more sets of collected non-environment data and/or analyses thereof. Thus, the environmental analysis module 22 may associate with the modeling engine 30 to apply analytics and/or AI/ML to the raw and/or analyzed data together or separate from data collected by sensors 100 configured to collect non-environmental or infant specific data and/or data analyzed by other modules. For example, the environment analysis module 22 may utilize data and/or analysis of one or more additional modules such as the sound analysis module 14, motion analysis module 16, vital analysis module 18, weight analysis module 20, evaluation module 40, sleep state analysis module 50, or combination thereof. Additionally or alternatively, the environment analysis module 16 may associate with the evaluation module 40 and/or condition identification module 60 to provide environmental data or analyses thereof according to an evaluation program or for identification of a condition.

As introduced above, the analysis unit 10 may include an evaluation module 40 configured to analyze collected data according to an active data collection scheme. The evaluation module 40 will typically be configured to include or execute one or more pre-defined evaluation programs designed to evaluate the infant. However, as the evaluation program may be intuitive based on analysis of collected data and/or via AI/ML, utilizing the modeling engine 30, the evaluation program may self-evolve over time. For example, as explained in more detail below, the evaluation module 40 may integrate with peripherals such as lights 210, graphical displays 220, tactile/haptic devices 230, speakers 240, evaluation objects 250, motor/actuators 260, or user interfaces 8 to measure voluntary or involuntary responses of a subject to various stimuli or conditions. In one example, an evaluation object 250 may undergo one or more motions in view of an infant to be evaluated. For example, a motor/actuator 260 may operatively associate with a 3D evaluation object 250 to cause movement of the evaluation object 250 or a graphical display 220 of an evaluation object 250 may display the motion. An optical sensor, such as a video camera 140a, may track the eyes or gaze of the infant. In a further example, a caregiver may be instructed to look at or speak to the infant during the motion. The data collected may be analyzed as part of an autism, object tracking, eye teaming, or other evaluation of the infant. In a further example, the evaluation program may change parameters of the evaluation object 250, such as size, color, rate of motion, or the type of evaluation object 250, used in the evaluation to further evaluate a deficiency or sufficiency of the infant. In some embodiments, the evaluation module 40 may include a catalog of evaluation programs to evaluate various developmental milestones, skills, and/or potential medical conditions with respect to the infant.

The analysis unit 10 may include a sleep state analysis module 50 configured to analyze sleep states of an infant such as identification of wake/sleep or sleep cycles. Utilizing one or more of motion data, respiration data, heart rate data, blood pressure, or sound data, the sleep state analysis module 50 may determine if an infant is asleep or awake. The wake/sleep data may be used to determine sleeping patterns. A sleep state may include identification of a particular sleep state phase and/or sleep stage. The sleep state analysis module 50 may also utilize the above collected data to identify sleeps cycles or patterns thereof. Sleep may be divided into two phases non-rapid eye movement (NREM) and rapid eye movement (REM). NREM sleep has 3 stages: N1-N3. N1 stage occurs right after falling asleep and is typically very short. During this N1 stage, the individual may be easily awakened and the stage is marked by alpha and theta waves and slowing of eye movements. N2 stage may include sudden increased brain wave frequency, sleep spindles or sigma waves, followed by a slowing or delta wave activity. N3 stage is deep sleep. An infant will spend about half of its sleep in REM sleep. REM sleep typically occurs after transitioning through N1, N2, N3, and back to N2. Progression through the sleep phases repeats throughout sleep. In some embodiments, analytics and/or AI/ML may be applied to the sleeping patterns to identify optimal sleep conditions and/or timing. The sleep state analysis module 50 may also analyze other collected data collected prior to, during, and/or after an baby is determined to be asleep to identify conditions affecting sleep time, depth, and/or duration, such as feeding, e.g., utilizing user feeding input data and/or weight data, ambient temperature data, motion data, e.g., motion of a platform upon which the baby is position, and/or ambient sound data. Artificial intelligence/machine learning may be further applied to generate outputs from correlation or patterns otherwise in the data.

The sleep state analysis module 50 may utilize data and/or analysis of one or more additional modules such as the sound analysis module 14, motion analysis module 16, vital analysis module 18, weight analysis module 20, environment analysis module 22, or combination thereof. For example, REM sleep is marked by deep unconsciousness, increased brain activity, and eyes may quickly jerk in different directions. REM sleep may be accompanied by increases in blood pressure and heart rate. Breathing may become shallow, irregular, and increase in frequency. Brief episodes of apnea may also occur. Dreaming occurs during REM sleep and the brain paralyzes muscles. Thus, motion data may be analyzed together with vital data, e.g., one or more of respiration, heartrate, blood pressure, or temperature, to identify sleep states. In some embodiments, the sleep state analysis module 50 may utilize the modeling engine 30 to apply analytics and/or AI/ML to provide sleep state analysis. In one example, sleep state analysis module 50 may utilize collected breathing data and heart rate data for sleep state analysis. The breathing data and/or heart rate data may be raw or analyzed. In a further example, the sleep state analysis also combines collected motion data. In one such example, analysis of the motion data includes application of video analytics.

As introduced above, in some embodiments, the analysis unit 10 may include a condition identification module 60 configured to identify medical conditions or events. The condition identification module 60 may utilize raw and/or analyzed data collected by the sensors 100 or input into the infant analysis system 1, which may include analyses generated by one or more of the sound analysis module 14, motion analysis module 16, vital analysis module 18, weight analysis module 20, environmental module 22, sleep state module 50, or evaluation module 40. The condition identification module 60, alone or together with the modeling engine 30 and/or evaluation module 40, may utilize a plurality of sensors 100, such as sound sensors 110, motion sensors 140, optical sensors such as video sensors 140*a*, infrared sensors 140*b*, or other image sensors, vibration sensors 140, and/or biological sensors, such as weight sensors 120*e*, to detect medical and/or developmental issues. The medical and/or developmental issues may include detection one or more of fever, fever precursors, abnormal breathing, type of abnormal breathing, cough, type of cough, vision abnormalities such as strabismus, seizures, seizure precursors, temperament of infant, hyperactivity, autism, or developmental delay. For example, the evaluation module 40 may execute a hearing evaluation program including output of various sound frequency and volume outputs from speakers 240. The condition identification module 60 may then identify one or more hearing conditions or conditions related to auditory response reflexes, if present. In one embodiment, the condition identification module 60 utilizes the modeling engine 30 in its analysis to identify issues with hearing or auditory response reflexes.

As introduced above, the modeling engine 30 may be configured to apply AI or other ML scheme to generate outputs such as predictions based on collected data and/or analyses generated by the various analysis modules. The modeling engine 30 may coordinate AI/ML output generation with the modules independently or in combination. AI/ML may be applied to raw and/or analyzed data, such as sound data, motion/movement data, wake/sleep or sleep cycle data, weight data, vitals data, environmental data, feeding data, or combination thereof.

Artificial Intelligence (AI) entails the development of computer systems capable of performing tasks that require human intelligence, such as visual perception, sound recognition, and decision-making. These tasks need cognitive functions associated with human minds, namely learning and problem solving. The modeling engine 30 may utilize one or more artificial intelligence levels such as reactive machine, limited memory, theory of mind, artificial narrow intelligence, artificial general intelligence, or artificial super intelligence. Deep learning (DL), for example is the one of the more accurate methods currently used in AI. Deep learning is a machine learning methodology that uses mathematical models called neural networks with large numbers of layers mimicking the human brain. Deep learning is able to extract complex hierarchal features and patterns present in large datasets. These features may then be merged together using neural networks to uncover the predictive model of the data. In various embodiments, the modeling engine 30 utilizes deep learning including one or more neural networks. In one example, the modeling engine 30 utilizes a convolutional neural network. The modeling engine 30 may utilize probabilistic methods such as Markov modeling, Kalman filters, or Bayesian networks. The modeling engine 30 may utilize supervised or unsupervised machine learning. In supervised learning, data examples along with their labels and annotations are used to train the modeling engine 30. For example, the modeling engine 30 may be configured to utilize support-vector networks to analyze data in supervised learning models. In unsupervised learning methods, data examples without labels and annotation may be used. In the unsupervised learning methods, the modeling engine 30 is configured to try to find a natural grouping of the data based on features present in the data.

Additionally or alternatively, the modeling engine 30 may be configured to generate analytics based on collected data and/or analyses generated by the various modules and/or submodules of the analysis unit 10. The modeling engine 30 may coordinate analytics generation with the modules or submodules independently or in combination. The modeling engine 30 may apply analytic modeling to identify patterns in the data and correlate the patterns to generate analytics based on the correlated patterns. The analytics may be applied to raw and/or analyzed data. For example, collected sound data corresponding to crying may be analyzed for patterns. The collected sound data corresponding to crying or patterns therein may be correlated to collected data related to vital states, conditions, evaluations, motion/movement, feeding, weight, environment, wake/sleep or sleep cycle data, or combinations thereof.

In some embodiments, the modeling engine 30 applies AI/ML to generated analytics. In this or another embodiment, the modeling engine 30 applies analytics to AI/ML outputs to provide useful predictive analysis.

As introduced above, one or more, including combinations, of the sound analysis module 14, motion analysis module 16, vital analysis module 18, weight analysis module 20, environment analysis module, or evaluation module 40 may be configured to apply AI or other ML, e.g., via a modeling engine 30, utilizing one or more data types or portions thereof. It will be appreciated that the modeling engine 30 may similarly apply AI or other ML schemes to collected data independent of the other various modules.

As introduced above, collected data may include data input by a user. A user interface 8 may be in communication with the analysis unit 10 to receive reports, evaluations, raw collected data, analyzed data, and/or suggestions or predictions, e.g., with respect to sleep timing, feeding timing, satiation state, sleep cycles, development, deficiencies, competencies, strengths, environmental conditions, medical conditions, or combinations thereof. The user interface 8 may allow a user to input data such as date of birth of an infant, gestation age at birth, medical conditions, family history, due date of an infant, name or an identifier for the infant, sex, weight, feeding information, and the like. The inputs may be used by the various modules and submodules for analyses and/or evaluations.

Additional inputs may include information inputs. Information inputs may include infant weights, infant lengths, infant circumferences, frequencies, travel, immunizations, illness, heart rate, respiratory rate, blood oxygenation, or the like. Infant weights may include weight at birth, infant weights at different weightings or over time, or the like. Infant length may include infant length at birth, infant length at different measurements or over time, or the like. Infant circumference may include limb, waist, or head circumference at birth, at different measurements or over time, or the like.

In various embodiments, the user interface 8 may be utilized to view or select various evaluation programs to be executed and/or to interact with the evaluation module 40 during execution of an evaluation program. For example, a user may view one or more evaluation programs or categories of evaluation programs and select one or more evaluation programs for execution by the evaluation module 40. The evaluation programs may be stored in a local or a remote database, such as database 300. In one example, when a user selects an evaluation program to be run, the evaluation module 40 calls a remote resource or database 300 for instructions for executing the selected program. The remote resource may be a central resource, which may be in the cloud.

The user interface 8 may be an integral part of the analysis unit 10 or a sleep device 5, or may be or be executed on a separate device, such as on a mobile peripheral device, which may be connected by a wired or wireless connection to the analysis unit 10, such as a computer, tablet, smartphone, or dedicated device. Wireless connection may include any suitable wireless protocol such as Wi-Fi, Bluetooth, nearfield, or RF, for example. The user interface 8 may include controls, set-up information input, and/or other features that may be utilized to input data to the analysis unit 10. Controls may include, for example, an on/off control, sound control, motion control, light control, temperature control, evaluation control, module task control, raw or analyzed data request controls, and/or controls for defining report topics and/or format.

In some embodiments, a user interface 8 may be provided as a mobile application. The mobile application may provide data inputs from the user to the analysis unit 10. The analysis unit 10 may provide data to the mobile application or another user interface 8. The data may include various forms of collected data, monitoring data, feedback data, control data, reporting data, evaluation data, analytics data, statistics, or the like. The mobile application may be installed on a mobile device. The device may be a computer, smartphone, tablet computer, dedicated device, or the like. The mobile device may have an operating system that may be iOS, Android, or other suitable operating system. The mobile application may enable interactions with the analysis unit 10. Interactions may include data input, defining operations of the analysis module, data requests, control instructions, or scheduling, as examples. Interactions may be enabled through the communication port 12. The communication port 12 may include a universal serial bus (USB) interface, Wi-Fi interface, Bluetooth interface, or other suitable interface for communicating with the user interface 8.

Interactions may include requesting, defining, execution, or presentation of reports, statistics, sharing or group interactions, benchmarking or comparison interactions, graphic interactions, acoustic signature of cry interactions, data upload to third party interactions, feedback from a subject matter expert interactions, warning alert interactions, overtone customization of white noise interactions, journal sharing/printout interactions, weight interactions, breastfeeding interactions, camera interactions, or the like. Other input interactions may include photo input interactions, video input interactions, or sound input interactions, for example.

In various embodiments, data collected by one or more respiration sensors 120d may be used by the condition identification module 60, which may also include operations of the vital analysis module 18, to detect respiratory conditions. For example, the vital analysis module 18 may analyze breathing and/or respiration patterns. Patterns may be compared to previous respiration patterns and/or patterns known to be indicative of one or more respiratory conditions. Respiratory issues that the condition identification module 60 may identify or predict utilizing respiration data may include, for example, cough, croup, or asthma. In one configuration, the condition identification module 60 together with the modeling engine 30 may utilize analytics and/or AI/ML with respect to respiration data to identify early on-set of an illness such as respiratory infections, colds, flu, respiratory syncytial virus, or Roseola. In one embodiment, such methodologies may utilize other collected data such as body temperature data or other data collected by biological sensors such as blood oxygen sensor 120a, heart rate sensor 120b, body temperature sensor 120c, electrodermal sensor 120f, or combination thereof. Sound data collected by sound sensor 110, e.g., data that may include breathing and/or infant vocalizations such as crying sounds, may also be input for analysis. In another or a further example, other collected data may include video data of the infant collected by video camera 140a, which may include infrared sensor 140b. The condition identification module 60 may be configured to identify any of the above or other respiratory conditions by comparing or inputting, e.g., into the modeling engine 30, respiration data including breathing and/or respiratory patterns in combination with other infant data and/or environmental data associated with the infant, such as fever state or body temperature (which may utilize regional body temperature or comparisons), body movements, cry analysis, or changes in sleep patterns.

As introduced above, infants have yet to develop many social and communication skills that may otherwise be useful to provide information regarding their health. This also makes it difficult to identify potential neurological conditions associated with an infant. However, it may be beneficial to identify such conditions early in order to provide early intervention. Indeed, early intervention of individuals with neurological conditions such as autism spectrum disorder is believed to significantly improve therapeutic and developmental outcomes.

In various embodiments, the condition identification module 60 may be configured to identify neurological conditions. For example, utilizing analysis of collected video data, such as by the motion analysis module 16, with or without additional collected data, which may include collected sound data and/or input data for example, the condition identification module 60 may be configured to identify neurological conditions. In one example, the condition identification module 60 analyzes collected motion and/or sound data to identify behavior states or responses such as video motion data including head, facial, and/or eye movements, sound data such as infant vocalizations while alone or during interactions with caregivers and/or objects for early detection of neurological conditions such as autism. The condition identification module 60 may utilize the modeling engine 30 to apply analytics or input collected data into one or more AI/ML models with associated algorithms for such analysis. In one example, video data of the infant collected by video camera 140a, which may include infrared sensor 140b, may be analyzed alone or together with collected sound data and/or situational data. For example, the collected data may be analyzed to identify head turn, smile, aversion of gaze, join attention, aversion of gaze, interest in objects over people, auditory ques, and/or dysphonic sounds for early identification of neurological conditions, such as autism. In one example, the condition identification module 60 may analyze collected data comprising video data and/or sound data to compare and/or identify lack of activities, facial expressions, and/or other ques. The analysis may compare observed eye movement to an expected eye movement model, such as to expected eye movement that tracks the mother of the infant or other caregiver over an object. Duration of fixation on an object may be tracked to identify if the duration taken for the infant to become bored with the object is within a predefined normal range. Video and/or motion data may also be analyzed for habitualization behavior indicative of autism. Additionally or alternatively, the condition identification module 60 may analyze collected data to identify physiological states or responses such as vital data collected by biological sensors 120 such as body temperature, respiration, galvanic skin response, heart rate, heart rate variability, and/or other collected data relating to physiological state or response of an infant to stimuli for early detection of neurological conditions such as autism.

As introduced above, the evaluation module 40 may be utilized while collecting the above collected data. For example, the evaluation module 40 may execute an evaluation program that causes speakers 240 to output predetermined or preselected sounds proximate to the infant. The data relating to the infant collected during the sound output may then be analyzed to identify conditions related to hearing or auditory response reflexes. The data may include video data alone or together with other data as noted above, such as sound data and/or vital data.

Evaluation programs configured to identify presence of autism or autism linked behaviors may include presenting an infant with social and non-social stimuli and analyzing collected data representative to the infant's response to the presented social and non-social stimuli. In one embodiment, the condition identification module 60 may coordinate with the evaluation module 40 to identify autism. For example, in addition to or in an alternative to data collection in spontaneous environments, the condition identification module 60 may utilize the evaluation module 40 to execute evaluation programs. According to one evaluation program, a mother or caregiver, i.e., an individual familiar to the infant, may be directed, via a user interface 8, speakers 240, graphical display 220, or otherwise, to respond in a certain way to the infant. For example, the mother or caregiver may be instructed to speak or look at the infant. Collected vital data such as heart rate and/or respiration data may then be analyzed for expected increases indicative of normal infant physiological response. The mother or caregiver may then be instructed to look away from the infant and then heart rate and/or respiration data may be analyzed for expected further increase indicative of normal infant physiological response. Additionally or alternatively, when the infant attempts to interact with the mother or caregiver, the mother or caregiver may be instructed to respond with a blank face or a smile. Physiological responses such as galvanic skin response, body temperature, and/or heart rate variability may be analyzed for comparison with expected normal measurements. Additionally or alternatively, behavior responses such as vocalizations and/or facial expression, head turn, smile, aversion of gaze, join attention, and/or aversion of gaze may also be analyzed for comparison with expected normal measurements. Measurements outside of the normal range may be considered indicative of autism or other neurological condition. One or more combinations of abnormal responses and/or degree of abnormality thereof may be used by the condition identification module 60. Additionally or alternatively, the mother or caregiver may be instructed to hold and evaluation object 250 in front of the infant within an immediate line-of-sight of the infant. Video data and/or sound data corresponding to the behavioral response of the infant and/or vital data corresponding to the physiological response of the infant may be collected and analyzed. In one embodiment, the video data is collected from a video camera 140*a* associated with the evaluation object 250 held by the mother or caregiver. Additionally or alternatively, a video camera 140*a* at another location may be used. In one embodiment, an evaluation object 250, such as a toy, operable to output sound, e.g., via a speaker 240, may be positioned in front of the infant within an immediate line-of-sight of the infant. If the evaluation object 250 or evaluation module 40, via operation of sensors 100, detect the infant smile, the evaluation object 250 or evaluation module 40 may cause the evaluation object 250 to output a predefined sound or pattern of sounds. The condition identification module 60 may then analyze the behavior and/or physiological response of the infant to the stimulus for responses indicative of autism or other neurological condition. In one embodiment, the condition identification module 60 may utilize the modeling engine 30 to identify or predict presence of autism or other neurological condition by inputting the raw or analyzed data collected during execution of the evaluation program for application of analytics and/or AI/ML.

As introduced above, the condition identification module 60 may analyze collected data corresponding to physiological response, such as one or more of body temperature, respiration, galvanic skin response, body temperature, heart rate variability and/or collected data corresponding to behavioral response such as sound vocalizations, to identify responses of the infant to sounds, such as sounds produced by a speaker 240 or evaluation object 250 that outputs sounds to identify neurological problems such as autism. As also noted above, analysis may include utilization of the evaluation module 40 and/or modeling engine 30. In one example, the voice of the mother or other caregiver may be output in the absence of the respective mother or caregiver and collected data corresponding to the behavior and/or physiology of the infant may be analyzed for behavior and/or physiological response indicative of autism or other neurological condition. In a further example, an unfamiliar voice may be presented and collected data from sensors 100 corresponding to the infant with respect to the output of the unfamiliar voice may be compared with collected data corresponding to the infant with respect to the output of the familiar voice. In one example, a mother or caregiver may be instructed to speak to the infant while wearing a mask in the line-of-sight of the infant. Collected data corresponding to the behavior and/or physiological response of the infant may be analyzed for behavior indicative of autism or other neurological condition. In a further example, the mother or caregiver may be instructed to similarly speak to the infant while not wearing the mask within the line-of-sight of the infant and the collected data corresponding to the behavior and/or physiological response of the infant may be compared with data collected corresponding to that which was collected when the mother or caregiver was wearing the mask. The comparative data may be analyzed for behavior and/or physiological response indicative of autism or other neurological condition. For example, in any of the above embodiments or examples, measurements outside of a normal range may be considered indicative of autism or other neurological condition. One or more combinations of abnormal responses and/or degree of abnormality thereof may be used by the condition identification module 60, which may include utilization of the modeling engine 30, to identify or predict autism or other neurological condition. In some embodiments, comparative scores of the infant on one or more evaluations or components thereof may be presented on a graphical display of a user interface 8. A report module 90 may output a report including identified conditions, predictions, probabilities, short or full scale scores and/or responses with respect to a plurality of evaluation metrics or batteries, advice, or raw and/or analyzed data. The report may be formatted for use by a parent or caregiver and/or a healthcare provider.

As introduced above, with respect to any of the above or below analyses, the analysis unit 10 may utilize the modeling engine 30 to apply analytics or input collected data into one or more AI/ML models with associated algorithms for the analysis of the collected data corresponding to evaluations and/or condition identification to generate probabilities and/or predictions with respect to identification of conditions and/or analytics derived from the execution of evaluation programs. For example, the evaluation module 40 may execute a hearing evaluation program including various sound frequency and volume outputs from speakers 240. The condition identification module 60 may then utilize the modeling engine 30 to identify issues with hearing or auditory response reflexes via analytics and/or AI/ML. In an above or a further example, the evaluation module 40 may execute one or more evaluation programs utilizing peripherals 200, such as lights 210, graphical displays 220, and/or evaluation objects 250, which may include, reflective surfaces, graphical displays 220, lights 210, and/or moveable patterns. Collected data, such as video data and/or physiological/vital data, collected during execution of the evaluation programs by corresponding sensors 100 may be analyzed. For example, collected video data may be analyzed to track eye movements of the infant as part of a predictive condition identification or diagnosis. Analysis of the collected video data may utilize the modeling engine 30 to apply video analytics and/or AI/ML models. In one example, the motion sensors 140 include one or more video cameras 140*a* located at a position around a platform upon which the infant is laid faceup or other evaluation space to capture video data of the eyes of the infant. The position may be directly over a head of the platform, approximately directly above the intended location of an infant's eyes when positioned on the platform. In one example, the video camera 140*a* is integrated with a mobile positioned or positionable above the platform. Additionally or alternatively, the mobile may be an evaluation object 250 and the analysis unit 10 may operatively control a mobile positioned or positionable above the platform. For example, in execution of an evaluation program, such as evaluation programs described herein for the identification of neurological conditions, reflex tracking or evaluation, and/or pupil tracking, the evaluation module 40, e.g., via communication with controller 400, may cause a motor/actuator 260 to drive motion of the mobile as part of the evaluation program. In one example, execution of the evaluation program causes the mobile to undergo various rotary motions. It will be appreciated that in various embodiments, the analysis unit 10 may perform any combination of the evaluations, identifications, and analyses described herein.

It is to be appreciated that when so equipped the evaluation module 40, sleep state analysis module 50, condition identification module 60, report module 90, and/or modeling engine 30 may communicate with and/or obtain analyzed data from one or more of the sound analysis module 14, motion analysis module 16, vital analysis module 18, weight analysis module 20, and/or environmental analysis module 22 to perform their respective operations described herein.

As introduced above, the analysis unit 10 may include or communicate with a report module 90. Results of the analyses performed by the analysis unit 10, e.g., by the various modules, submodules, and/or modeling engine 30 thereof, may be formatted and/or output in one or more reports available via the report module 90. A report may include one or more graphical representations of collected data, such as graphs or charts. The representations may include single or multiple instant analyses and/or evaluations. The representations may depict raw and/or analyzed collected data overtime. The representations may include single or multiple collected data categories and/or evaluation batteries that may be used to visualize relative changes observed overtime. Additionally or alternatively, the report may depict or identify what data is changing, why it is happening, what the caregiver may expect to arise in the future with and/or without intervention, tips or tricks to treat or address issues or deficiencies, and/or advice regarding intervention steps. In one example, the report may depict or identify changes in the data such as sleep regression.

The report module 90 may output scores and/or confidence intervals with respect to one or more conditions identified by the condition identification module 60. As noted above, the condition identification module 60 may utilize the evaluation module 40 to execute evaluation programs configured to assist in obtaining data for analysis related to identification of conditions and/or modeling engine 30 to apply analytics and/or AI/ML to collected data. In one example, the report module 90 outputs confidence intervals with respect to one or more conditions such as high risk, moderate risk, low risk, or undetected. The report module 90 may output various scores or confidence intervals with respect to categories, batteries, and/or components of a composite score used to identify conditions.

The report module 90 may be configured to include or output reports comprising raw data, analyzed data, predictions, conditions identified by the analysis unit 10, evaluation data, historical or archival data relating to the same, or combinations thereof. The report module 90 may include or access a database 300 including such data.

The user interface 8 may be operable to allow users to specify a report type, format, and/or items to be included in the report. The user interface 8 may be operable to allow a user to specify one or more recipients of a report or category of reports. The user interface 8 may allow a user to specify report recipients as a discrete instance, according to a defined schedule, or on an ongoing basis. Reports may be provided in an email or other electronic communication, for example. In an above or another example, the report module 90 may comprise a network accessible, e.g., internet accessible, secure platform into which parties approved by a user may access to view reports. The secure platform may be available through a secure, e.g., password protected, website. In some embodiments, users may select among multiple categories of reports including predefined categories of data, evaluations, predictions, and/or analyses to be available or transmitted to identified recipients, such as a physician/pediatrician and/or nurse.

As introduced above, the report module 90 may access database 300. The database 300 may include an historical or archival database including raw and/or analyzed data output to the database 300 by the analysis unit 10. In some embodiments, sensors 100 may also transmit raw data directly to the database 300.

In one embodiment, the report module 90 may submit reports to a central resource that collects reports from multiple infant analysis systems 1 for the purpose of population data analysis and/or improvement of analytics or AI/ML models, which may be used to update models and/or algorithms used by the modeling engine 30.

In some embodiments, the report module 90 may be configured to provide reports to medical caregivers such as physician/pediatrician or nurse. For example, users may specify via a user interface 8 a medical caregiver to which one or more reports are to be provided or be made accessible. Thus, the report module 90 may be used to supply historical information to a medical caregiver, such as vital/physiological data (e.g., temperature data, respiration data, heart rate data, weight data), evaluation data, condition identification data (e.g., identified conditions or deficiencies, predictions, analytics), and/or sleeping patterns, to name a few, to assist with medical care and/or diagnosis of the infant. For example, in some embodiments, the report module 90 may be used to supply analyzed data, which may include evaluation data such as identified conditions, predictions, and/or analytics, to medical caregivers. In one example, a medical caregiver may specify one or more evaluation programs to be executed by the evaluation module 40. In an above or further embodiment, the evaluation module 40 may be configured to receive, from a central resource or medical caregiver, new or update current evaluation programs. When applicable, the evaluation programs may include or specify analytic and/or AI/ML models for use by the modeling engine 30 in analysis of collected data associated with execution of the evaluation programs.

As introduced above, the analysis unit 10 may be configured to collect and analyze data for use by parents or caregivers. The analysis, which may be presented to a user interface 8 and/or in a report via the report module 90, may provide advice for further skill development, medical or developmental conditions to consider or watch, feeding schedules, or sleep schedules, for example. In one application, the analysis unit 10 utilizes the modeling engine 30 to analyze data related to sleep behavior. The analysis unit 10 may output data, recommendations, and/or predictions derived therefrom corresponding to one or more of feeding times favorable or unfavorable for inducing or prolonging sleep, which may include related sleep quality and/or duration; feeding volume favorable or unfavorable for inducing or prolonging sleep, which may include related sleep quality and/or duration; satiation analysis with respect to sleep quality and/or duration; weight changes relating to sleep quality and/or duration; vital sleep analysis such as blood oxygen, heart rate, body temperature, respiration rate, respiration depth before, during, or after sleep, which may include related sleep quality and/or duration; infant motion prior to or during sleep, which may include related sleep quality and/or duration; sleep platform motion favorable or unfavorable for inducing or prolonging sleep, which may include related sleep quality and/or duration; infant sounds prior to, during, or after sleep, which may include related sleep quality; environmental sounds, lighting, and/or temperatures favorable or unfavorable for inducing or prolonging sleep such as sound or parameters of sound generated by speakers 240 such as various white noise parameters and which may include related sleep quality and/or duration; or combination thereof. The analysis may include analytics and/or AI/ML provided by the modeling engine 30. A report comprising the modeling engine 30 output, or data derived therefrom, or subsequent analysis of the output, if any, may be transmitted to or otherwise be accessible to users via the report module 90 and/or user interface 8. The report may include advice to caregivers/parents regarding one or more of optimal or preferred sleep times with respect to depth of sleep, sleep patterns, and/or sleep duration, tips and tricks specific for the situation, e.g., engaging parent/caregiver in adjusting sound or motion settings of a sleep device 5 to increase sleep quality or timing, changing temperature of a room or environment in which the infant sleeps, modification of feeding schedule and/or feeding volume, modification of lighting, or combinations thereof.

In any of the above or another embodiment, the analysis unit 10 may utilize the modeling engine 30 to apply AI/ML to identify changes in behavior of an infant to support the parent or caregiver. In one embodiment, the modeling engine 30 may compare sets of historical collected data related to one or more data categories such as sleep, respiration, temperature variations, and/or other patterns with a current set of collected data in corresponding data categories. The analysis may include comparing analyzed data with respect to the data sets. A report of the analysis may be output or available via the report module 90 and/or user interface 8. The report may depict or identify what data is changing, why it is happening, what the caregiver may expect to arise in the future with and/or without intervention, and/or advice regarding intervention steps. As introduced above, such changes may include sleep regression.

As introduced above, the infant analysis system 1 may include, e.g., be integrated with, communicate with, or be operable together with a sleep device 5. In one example, the sleep device 5 is a standalone speaker with controllable sound output that may be positioned proximate to an infant to promote sleep, relaxation, or otherwise. In a further example, the sleep device 5 includes a bassinet or crib. In a further example, the bassinet or crib may have a movable platform upon which an infant is to be positioned.

The sleep device 5 may be configured to output various stimuli such as one or more of sound and/or motion of a sleep platform. In one example, the sleep device 5 is similar to that described in U.S. patent application Ser. No. 14/448, 679, filed Apr. 31, 2014, or U.S. patent application Ser. No. 15/055,077, filed Feb. 26, 2016, both of which are incorporated herein. In some embodiments, the sleep device 5 may be considered a peripheral device 200 that may be controlled by controller 400. Sound outputs of the sleep device 5 may be output by one or more speakers which may be the same or different than speakers 240 described above. Motion of the platform may be caused by one or more actuators or motors, which may include or be in addition to motor/actuator 260 described above, configured to cause the platform to move. Movements may include one or more of linear head-to-toe or side-to-side motion, side-to-side tilting along an axis that extends longitudinally through the platform or proximate thereto. The controller 400 may be integrated with the sleep device 5 or may be separate and configured to operatively control operations of the sleep device 5, peripherals 200, sensors 100, and/or operations of the analysis unit 10. In some embodiments, the infant analysis system 1 includes, e.g., integrates with, or may communicate with lighting 210, temperature control devices 270 (e.g., fans, heaters, air coolers), or other environmental control devices to control the same via the controller 400. As noted above, in some embodiments, the analysis unit 10 may include or be operable to communicate or control, via controller 400, peripheral devices 200 such as lights 210, speakers 240, graphical displays 220, tactile/haptic devices 230, evaluation objects 250, temperature control devices 270, and/or motor/actuators 260. In some embodiments, such peripheral devices 200 maybe associated with a sleep device 5. For example, the controller 400 may be configured to control sound output from a speaker 240 and/or control operation of an actuator/motor 260 for moving a sleep platform. In various embodiments, the analysis unit 10 may be in wired or wireless communication with the controller 400 and may be operable to control lighting, sound outputs, platform movements, temperature, and/or environmental conditions via the controller 400.

In some embodiments, the infant analysis system 1 may be configured to generate and execute smart response instructions. Smart response instructions may be generated by the analysis unit 10 for execution by the controller 400. It is to be appreciated that the controller 400 may include one or more separate or integrated controllers that may interface with sensors 100, peripherals 200, sleep device 5, user interface 8, database 300, and/or analysis unit 10 to execute smart response programs to generate smart responses identified or defined by the analysis unit 10. In some embodiments, the analysis unit 10 may transmit collected data, analyzed data, instructions, programs, and/or reports to the controller 400. For example, the analysis unit 10 may transmit smart response programs for execution by the controller 400 to optimize responses to collected data, which may include analyzed data. In some embodiments, the controller 400 may additionally or alternatively receive collected data directly or indirectly from sensors 100. The analysis unit 10 may transmit smart response instructions to the controller 400 to cause the same to output stimuli according to the smart response instructions. Example stimuli outputs may include initiation, modification, or termination of temperature modulated by temperature control device 270, motion of a platform modulated by motor/actuator 260, sound output from speakers 240, lighting modulated by lights 210, and/or displays modulated by graphical display 220.

In one example, the analysis unit 10 may utilize the modeling engine 30 to apply AI/ML to identify an infant's need for sound stimulation and/or movement stimulation from a platform of a sleep device 5 to optimize stimulation versus time to sleep. Additionally or alternatively, the analysis unit 10 may utilize the modeling engine 30 to apply AI/ML to identify optimal responses, e.g., smart responses for smart response instructions, with respect to sound output and/or movement stimulation of a platform of a sleep device 5 to encourage the infant to stay asleep or continue sleeping. The analysis may include, for example, analysis of collected data corresponding sleep patterns, heart rate, respiration rate, respiration depth, infant motion, sleep platform motion, infant sounds, environmental sounds, sounds generated by speakers such as various white noise parameters, or combination thereof. A report of the analysis may be output or available via the report module 90 or user interface 8. In some embodiments, the report may be transmitted to the controller 400. The report may include or define a sleep program, which in one example may include or accompany smart response instructions, that optimizes stimulation versus time to sleep. The report may include or define a sleep program that optimizes platform movement and/or sound outputs to the infant in responses to one or more of raw collected data and/or analyses thereof. For example, the controller 400 may receive raw or analyzed collected data from the analysis unit 10 and/or raw collected data directly from sensors 100. In some examples, the data may identify a trigger for a smart response defined by a smart response program and/or instruction thereof.

In an above or another example, the analysis unit 10 may utilize the weigh analysis module 20 and the modeling engine 30 to apply AI/ML to collected weight data to identify when an infant needs to be fed. The analysis may include, for example, analysis of collected weight data overtime. The above analyses may include comparison of historical weight data tracked overtime, which may include time of day and current weight data. In further embodiments, the analysis further includes data sets of weight data tracked overtime for a population of infants. The analysis unit 10 may include or access such population data sets in a local or remote database, such as a central resource or cloud. In some embodiments, population data may be provided to the analysis unit 10 and/or database 300 via data updates. In some applications, the analysis unit 10 may further utilize the sound analysis module 14 to analyze collected sound data corresponding to cries with analytics and/or AI/ML provided by the modeling engine 30, as described in more detail below, together with collected weight data and/or analysis thereof to identify when an infant is underfed or should be fed. When the analysis unit 10 identifies that the infant is underfed or should be fed, a smart response may be triggered. For example, the analysis unit 10 may generate a notification output to a user interface 8, such as to a display panel of the sleep device 5 or to an application executed on a user smart device, computer, or dedicated device to inform the user that the infant may be underfed for optimal sleep. The notification may provide an amount or duration of feeding that may be followed to promote sleep and/or growth. In a further example, the notification may be or include a report generated by the report module 90 that provides raw collected weight data or analysis thereof overtime and may further include steps that a user may take to achieve satiation. In one embodiment, the report or notification may provide a suggested feeding schedule. The report or notification may provide suggested feeding times and/or amounts of food to be provided during multiple intervals of a day. The report or notification may provide suggested amounts and/or types of food to feed the infant based on time of day or events such as following or preceding a nap of a duration range.

In an above or another example, the analysis unit 10 may utilize collected weight data to detect dehydration. For example, the condition identification module 60 may utilize the weight analysis module 20 and the modeling engine 30 to apply AI/ML to identify when an infant may be dehydrated. The above analyses may include comparison of historical weight data tracked overtime, which may include time of day and current weight data. In further embodiments, the analysis further includes data sets of weight data tracked overtime for a population of infants. The analysis unit 10 may include or access such population data sets in a local or remote database, such as a central resource or cloud. In some embodiments, population data may be provided to the analysis unit 10 and/or database 300 via data updates. In any of the above or other embodiments, other collected data such as one or more of temperature data (e.g., collected by temperature sensor 120*c* or infrared sensor 140*b*), skin turgor data (e.g., collected by video camera 140*a*), skin conductivity data or impedance (e.g., collected by electrodermal sensor 120*f*), user input regarding feeding amounts or times, or cry analysis may be used alone or in combination, collected weight data to identify when an infant may be dehydrated. When the analysis unit 10 identifies dehydration, a notification may be transmitted to a user interface 8, such as to a display panel of the sleep device 5 or to an application executed on a user smart device, computer, or dedicated device to notify the user of the dehydration. The notification may provide an amount or duration of feeding or hydrating fluids to provide the infant, which may include a suggested schedule for the user to follow.

As introduced above, the condition identification module 60 may be configured to analyze collected data to detect medical conditions or events. For example, the condition identification module 60 may utilize raw motion data or motion data analysis associated with the infant, e.g., data analysis performed by the motion analysis module 16, to identify seizure events and/or precursors to seizure events. In a further example, raw or analyzed motion data or analysis is utilized with the modeling engine 30 to apply AI/ML analysis to identify a seizure event and/or precursors to a seizure event. Motion data analyzed may include video, accelerometer, vibration, or other movement data corresponding to kicking and other body movements indicative of a seizure. Analysis may consider movement frequency, amount of local movement of the infant with respect to head, arms, legs, feet, hands, torso, and/or facial regions, total combined movement at multiple such locations, and/or other movement characteristics. In some examples, analysis may consider other collected data such as data input by a user such as medical history, e.g., birth weight, pregnancy duration, pregnancy or birth complications, medical conditions, and the like. When the condition identification module 60 identifies a seizure or precursor to a seizure, the analysis unit 10 may initiate a notification to be transmitted to a user interface 8, such as to a display panel of the sleep device 5 or to an application executed on a user smart device, computer, or dedicated device. The notification may include an alarm or call to an emergency care provider.

In one embodiment, the condition identification module 60 may be configured to identify strabismus. The condition identification module 60 may analyze collected image data of the eyes of an infant at various times and in response to various stimuli to determine if the infant has strabismus. In one embodiment, the condition identification module 60 may identify a type of strabismus such as exotropia, marked by eye divergence, esotropia, marked by eye convergence; or hypertropia, marked by vertical misalignment. In on example, image data of light reflecting from an infant's eyes are collected and analyzed for alignment with pupils.

In some embodiments, utilizing image data of the infant's eyes collected in response to varied visual stimuli, the condition identification module 60 may identify whether the strabismus condition is comitant or incomitant. For example, an evaluation object 250, displayed image, or light 210 may be positioned at various angles relative to the gaze of the infant and collected image data may be analyzed to determine whether the strabismus condition varies by direction of gaze.

As introduced above, in one example, the condition identification model 60 may utilize the evaluation module 40 to identify strabismus or other eye conditions. For example, an evaluation object 250 is used and a video sensor 140a or other image capture device may collect image data of the infant's eyes, e.g., relative orientations of the eyes of the infant or direction of gaze, as the infant gazes at and/or tracks the evaluation object 250. In one configuration, the video sensor 140a is housed in or couplable to the evaluation object 250. In one example, the evaluation object 250 includes or is incorporated in a mobile configured to be positioned over the infant to attract the gaze of the infant. In another or further example, a video sensor 140a collects image data of an infant's eyes as the infant tracks and/or focuses on images on a graphical display 220. The images may include, for instance, moving images and/or images moving into and out of focus. In another or further example, one or more lights 210 are presented to the infant and the video sensor 140a collects image data with respect to the relative orientations of the eyes of the infant or direction of gaze as the infant looks at and/or tracks the one or more lights 210.

In one embodiment, the condition identification module 60 utilizes the modelling engine 30 to identify strabismus, which may be together or separate for identification and/or evaluation incorporating the evaluation module. For example, image data may be collected in response to an evaluation program or over time in response to the environment for analysis. In one configuration, the modelling engine 30 applies AI/ML, utilizing the image data as input into an algorithm trained on image data of a population of infants. For example, the modeling engine 30 may be configured to perform a population comparison and monitor (intermittent, prolonged, changes) over time using AI/ML. In one configuration, the condition identification module 60, utilizing the modelling engine 30, monitors collected image data over time. For instance, the algorithm may be trained on population data wherein the input image data is compared to data collected from a static population or the algorithm may be trained on population data collected over time wherein the infant image data is similarly collected over time for analysis on an intermittent or prolonged basis and input into the algorithm for monitoring changes over time on such basis. In some examples, additional data may be included such as collected data, analyzed data, and/or input data. For instance the algorithm may receive inputs such as motion data, gestation age at birth, medical conditions, or family history.

In one embodiment, the condition identification module 60 may be configured to identify sudden infant death syndrome (SIDS) events or precursor events. For example, utilizing a combination of collected data corresponding to one or more of respiration, heart rate, facial expressions, or infant motion, the condition identification module 60 may be configured to identify conditions indicative, accompanying, or predictive of a sudden infant death syndrome (SIDS) event. The condition identification module 60 may also utilize the modeling engine 30 to apply analytics and/or AI/ML to such collected data to identify conditions indicative, accompanying, or predictive of a sudden infant death syndrome (SIDS) event.

The condition identification module 60 may also be configured to track all or portions of collected data collected overtime and utilize the modeling engine 30 to apply AI/ML to detect unexpected or anomalous changes from previous data or analyses. For example, analyses of collected data may correspond to particular behaviors and unexpected changes in such behaviors may indicate the presence of a condition or precursor of the condition. In some embodiments, the raw or analyzed collected data is tracked overtime and AI/ML is used to compare historical data with current collected data, which may also be compared to population data to identify potential conditions. The population data may include data obtained from a population of infants in which the data is considered normal or expected. In these or further embodiments, the historical and current collected data may be compared to that of data from a population of infants in which the data is considered abnormal or associated with one or more conditions. Comparisons with such abnormal populations indicating similar trends in the compared data may be used to identify the presence of a similar condition in the infant.

The analyses performed by the analysis unit 10 may include behavior analyses. Behavior analyses may include analysis of combinations of collected and/or analyzed data. For example, weight analyses may be combined with analyses of motion, physiological/vitals, and/or environmental data. Behavior states may include one or more of hungry, tired, bored, unwell, content, agitated, asleep, or combinations and/or levels thereof. For example, weight data, motion data, and sound data may be analyzed to identify an infant that is in a hungry agitated state. The analysis may further identify a level of hunger and/or agitation.

Behavior state analyses may be utilized by the analysis unit 10 to identify behaviors and generate response instructions, which may include smart response instructions, that when executed by the system cause output of one or more response stimuli with respect to the infant to achieve a more desirable behavior state, such as a content state or an asleep state. For example, the analysis unit 10 may operatively communicate analyses or operation instructions to the control system 400. The control system 400 may be configured to control operation of an actuator/motor operable to move a platform of a sleep device 5, a speaker 240 to output sound such a white noise or low pitch rumbling, a light 210 to increase or decrease lighting, and/or a temperature control device 270 to modify environmental temperature according to the response instructions. The response instructions may be preprogramed to initiate upon receipt of a specified analysis or may be provided to the controller 400. The analyses or response instructions may cause the controller 400 to cause a peripheral 200 to execute a specified response stimuli such as causing a motor/actuator operable to move a platform of a sleep device to apply one or more specified motion characteristics to the platform, e.g., frequency, amplitude, duration of motions and/or levels or sequences thereof, tailored to transition the infant from the current behavior state identified by the analysis to another behavior state. For example, if the behavior analysis indicates the infant is in a tired state, the response instructions may specify gentle movement of the platform in a side-to-side motion pattern. When the sleep system 1 also includes speakers 240 for outputting sound output, response instructions may also include instructions for sound output in addition to motion output and may be similarly tailored to transition the infant from a current behavior state to another behavior state. For example, the instructions may also specify white sound to be output from the speaker 240. If the behavior state analysis indicates that the infant is in a tired agitated state, the response instructions may specify enhanced side-to-side or jiggling motion of the platform. Similarly, when the infant analysis system 1 also includes other environmental control peripheral devices 200, response instructions may include modification of corresponding environmental stimuli (e.g., lighting, temperature) in addition to or instead of one or both of motion or sound. When an analysis identifies behavior states that are unlikely to be soothed or otherwise suitably addressed through initiation, termination, or modification of motion, sound, lighting, temperature, and/or other environmental stimuli, e.g., when a behavior state analysis identifies an elevated hunger state, the analysis unit 10 may generate or cause a notification to be transmitted to a user interface 8 to notify a caregiver. The notification may notify the user or caregiver that the infant is hungry. In one example, the notification provides a suggested amount or duration of feeding. In another or a further example, a user or caregiver may access the user interface 8 a specify a desired behavior state and the infant analysis system may provide a suggest feeding schedule, e.g., amount, duration, timing, along with one or more additional instructions such as an activity and/or duration of activity or further steps and/or setting with respect to a sleep device 5 and/or peripherals 200 to transition the infant to the desired behavioral state.

In some embodiments, the analysis unit 10 compares behavior state analyses prior to initiation of a response instruction and after initiation of a response instruction, which may include multiple time points or ranges of time after initiation, to learn how particular stimulation or combinations of stimuli affect particular or combinations of behavior state characteristics. In some embodiments, the evaluation module 40 may be configured to cause modification of sound out from speaker 240, platform movement of the sleep device 5, and/or other environmental stimuli to allow the analysis unit 10 to learn from the collected data corresponding to an infant's response to the modification. For example, sound output volume, lighting, and/or platform motion patterns or characteristics thereof (e.g., motion type such as up-down or side-to-side and/or motion characteristic such as frequency and/or amplitude) may be changed and infant response may be identified in order to learn from the response. When applied, AI/ML may be supervised or unsupervised. In one embodiment, data collected from a plurality of infant sleep systems may be collected and analyzed by unsupervised AI/ML to identify cries with similar attributes that can be similarly classified.

Infants cry and vocalize in different ways. Such cries and vocalizations also differ among populations of infants. For example, some infants grunt or cry loader, quieter, longer, shorter, or have different cry cadences, than other infants. Individual infants may also cry differently according to the reason for crying, such as in response to hunger, tiredness, fatigue, boredom, frustration, illness, fright, constipation, or lack of comfort. In various embodiments, the sound analysis module 14 may be configured to perform cry analysis. Cry analysis may include analysis of characteristics of cries detected by one or more sound sensors 110. In various embodiments, cry analysis by the sound analysis module 14 utilizes AI/ML, e.g., via the modeling engine 30, to unwrap the nuances of an infant's cries. For example, the sound analysis module 14 may identify a cry in collected sound data and/or sounds originating from inside a sleep device 5 or otherwise from an infant to be analyzed. Such sound data may be filtered or raw. For example, in one embodiment, the sound analysis module 14 may filter out sounds not originating from the infant. In these or other embodiments, the sound analysis module 14 may additionally or alternatively receive raw sound data that has not been filtered or analyzed for sound location and/or positive identification of a cry. Characteristics measured in the sound data may include loudness or amplitude, frequency, wavelength, or duration, for example. Other characteristics may also be measured such a sound patterns or cadence. The analysis may provide information regarding a behavior state and/or medical or environmental condition of the infant or its surrounding environment. The analysis may be used to distinguish between whether the infant is hungry, unwell/ill, uncomfortable, content, satiated, bored, or tired, for example. In one example, the analysis starts with a baseline cry to differentiate between cries and grunts. In another or a further example, the sound analysis module 14 generates a cry algorithm that is personalized to the infant. For example, the algorithm may identify values or value ranges in measured characteristics based on previous analyses that are specific to the infant and its behavior states. The cry algorithm may be generated together with the modeling engine 30. For example, collected sound data may be input into an AI/ML cry algorithm and the modeling engine 30 may output a prediction of a behavior state and/or condition associated with the infant and/or the environment of the infant. In one example, a user may observe the infant and enter a perceived behavior state or environmental condition that the modeling engine 30 may use to learn the specific nuances of the infant's cries. In another or a further example, the modeling engine 30 may access database 300 or a central resource or cloud to receive cry algorithm updates and/or to store raw and/or analyzed sound data that may be used to generate updated cry algorithms specific to the infant, an infant population, or subset of an infant population.

In some embodiments, cry analysis by the sound analysis module 14 may include analysis of other collected data, such as motion data with respect to the infant, weight data, and/or biological data, which may include vital data and/or physiological data, or analyses thereof with respect to the infant. For example, motion data may identify high intensity kicking or other motions useful for calculating behavior state in conjunction with the sound analysis. The additional data or analysis thereof may be analyzed together with sound data.

The sound analysis module 14 may further utilize the modeling engine 30 for cry analysis to apply analytics and/or AI/ML to the collected data. For example, collected data included in the analysis in addition to sound data may include one or more collected input data and/or collected sensor data, such as motion data, environmental data (e.g., temperature), time of day, age of infant, birth weight, video data (gross movement, movements of particular body parts, rate of movement, color changes in face or flushing), breathing data (frequency, depth, pauses, or pause durations), weight data, physiological data (e.g., body temperature, skin conductance, blood pressure), and/or situational data such as time since last feeding, amount of food consumed over one or more predetermined periods of time, time since last sleep, duration of last sleep, duration of sleep within a previous predetermined period of time, and/or quality of sleep. The collected data may be input into the cry algorithm for application of AI/ML and output of a predicted behavior state and/or condition determined from the same.

In some embodiments, the sound analysis module 14, utilizing the modeling engine 30, analyzes collected values for one or more cry characteristics to identify nuances and/or emotional factors related to the infant. For example, grunting may be identified with respect to the infant. Previous cry analyses may indicate that similar grunting sounds have been associated with one or more levels of hunger states, sleep states, tired states, content states, bored states, unwell states, or other behavioral states.

As introduced above, the sound analysis module 14 may perform cry analysis utilizing the modeling engine 30 to apply analytics and/or AI/ML to characterize cries, which may include identification of a current behavior state. In further embodiments, the analysis unit 10 may utilize the modeling engine 30 to apply analytics and/or AI/ML to identify or generate smart response instructions with respect to operation of a sleep device 5 and/or peripherals 200. A goal of the smart response instructions may be to transition the infant to or otherwise achieve a desired behavior state. For example, a smart response instruction goal may be to soothe, promote initial sleep, promote returning to sleep, or promote continued sleep. Thus, the cry analysis may be used in combination with analytics and/or AI/ML to characterize cries to determine behavior states and/or to identify or generate a smart response instruction that specifically responds to a behavior state for transitioning the infant to another desired behavior state. As noted above, the cry analysis may include data other than collected sound data, such as collected motion data, weight data, biological data, which may include vital data and/or physiological data, and/or environmental data. The modeling with the cry algorithm may compare or consider previously collected raw or analyzed collected data and how the data changed in response to one or more stimuli. The stimuli may be stimuli output by peripherals 200 or external stimuli within the environment detected by sensors 100. The stimuli may include one or more of motion characteristics of a sleep platform (amplitude, frequency, acceleration, deceleration, duration of motion characteristics, sequence of motion characteristics), sound characteristics (frequency, amplitude, wavelength, tone, melody, sound type), lighting (wavelength, intensity, duration of light characteristics, sequence of light characteristics), temperature (which may include humidity), and/or other stimuli. Thus, cry analysis may analyze measured cry characteristics and, based on analysis of the infant's previous behavioral response to one or more motions, sounds, lighting, temperature, other environmental stimuli, or levels and/or sequences thereof, the analysis unit

10 may cause the controller 400 to initiate smart response instructions with respect to peripherals 200 and/or a sleep device 5. The smart response instructions may tailor platform motions and/or sound outputs to soothe, relax, or induce sleep, for example. The analyses may characterize a level of agitation that may, based on analysis of previous behavior states and stimuli response, correspond to a response setting to achieve an optimal response corresponding to a desired behavior state. For example, the cry analysis may characterize cry behavior, loudness, and intensity and the analysis unit 10 may identify an optimal stimuli response to the analysis to achieve the desired behavioral state. When cry analysis identifies behavior states that are unlikely to be soothed or transitioned to a more desirable behavioral state through initiation or modification of motion, sound, lighting, temperature, and/or other environmental stimuli, e.g., when a cry analysis identifies an elevated hunger state, the analysis unit 10 may generate or cause a notification to be transmitted to a user interface 8 to notify a caregiver.

The analysis unit 10 may be configured to continue infant analyses while stimuli is output by the sleep system according to response instructions, which may include smart response instructions. The further analysis, such as continued cry analysis or other behavior state analysis, may identify updated behavior states that may be used to update response instructions to tailor the stimuli output to the updated behavior states. For example, if the infant is determined to have transitioned to a lower agitation state, the intensity of sound or motion may be reduced if the analysis unit 10 determines that such reduction is consistent with achieving the desired behavior state. In another example, when behavior or cry state analysis determines that an infant will not go back to sleep, e.g., based on analysis of crying, the analysis unit 10 may instruct or cause the controller 400 to terminate stimulation and may initiate a notification to a user interface 8 to notify the caretaker as quickly as possible.

While the present description generally describes application of the infant analysis system to infants, those having skill in the art will appreciate that the systems, methods, and associated features described herein may be equally applicable to other population segments such as toddlers, adolescents, mentally retarded, handicapped, adults, or elderly individuals.

The systems and methods described herein may be executed by hardware or be imbodied in software stored in memory and executable by hardware. For example, the methods and systems described herein may include a memory that stores instructions, and processor that executes the instructions to perform the operations described herein. The present disclosure may include dedicated hardware implementations including, but not limited to, application-specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example network or system is applicable to software, firmware, and hardware implementations. As used herein "transmit" means that data or representation of the data is transmitted by wire, wirelessly, or is otherwise made available to the receiving component, e.g., process, algorithm, module, operator, engine, generator, controller, or the like. In some examples, data transmitted to a receiving component may be transmitted to another component or database wherein the data may be further transmitted to the receiving component or otherwise made available to the receiving component. Thus, data transmitted by a first component/processing module to a second component/processing module may be directly or indirectly transmitted. In one example, data may be transmitted by the transmitting component or another component to a receiving component by transmitting an address, location, or pointer to the data stored in memory, such as one or more databases.

In accordance with various embodiments of the present disclosure, the processes described herein may be intended for operation as software programs running on a computer processor. Furthermore, software implementations can include but are not limited to, distributed processing or component/object distributed processing, parallel processing, or virtual machine processing that may be constructed to implement the methods described herein.

The present disclosure describes various systems, modules, units, devices, components, and the like. Such systems, modules, units, devices, components, and/or functionalities thereof may include one or more electronic processors, e.g., microprocessors, operable to execute instructions corresponding to the functionalities described herein. Such instructions may be stored on a computer-readable medium. Such systems, modules, units, devices, components, the like may include functionally related hardware, instructions, firmware, or software. For example, modules or units thereof, which may include generators or engines, may include a physical or logical grouping of functionally related applications, services, resources, assets, systems, programs, databases, or the like. The systems, modules, units, which may include data storage devices such as databases and/or pattern library may include hardware storing instructions configured to execute disclosed functionalities, which may be physically located in one or more physical locations. For example, systems, modules, units, or components or functionalities thereof may be distributed across one or more networks, systems, devices, or combination thereof. It will be appreciated that the various functionalities of these features may be modular, distributed, and/or integrated over one or more physical devices. It will be appreciated that such logical partitions may not correspond to the physical partitions of the data. For example, all or portions of various systems, modules, units, or devices may reside or be distributed among one or more hardware locations.

The present disclosure contemplates a machine-readable medium containing instructions so that a device connected to the communications network, another network, or a combination thereof, can send or receive voice, video or data, and to communicate over the communications network, another network, or a combination thereof, using the instructions. The instructions may further be transmitted or received over the communications network, another network, or a combination thereof, via the network interface device. The term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure. The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or re-organizing any of the disclosed steps, components, elements, features, aspects, characteristics, limitations, and the like, of the various non-limiting and non-exhaustive embodiments described in this specification.

Various elements described herein have been described as alternatives or alternative combinations, e.g., in lists of selectable components, features, modules, sensors, peripherals, etc. It is to be appreciated that embodiments may include one, more, or all of any such elements. Thus, this description includes embodiments of all such elements independently and embodiments, including such elements in all combinations.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" corresponds to "x and/or y" and refers to "x", "y", or both "x" and "y", whereas "either x or y" refers to exclusivity.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments could be modified, reduced, or enhanced without departing from the scope and spirit of the claims described below.

What is claimed is:

1. An infant analysis system, the system comprising:

a plurality of sensors positioned relative to a sleep device to collect data with respect to an infant when positioned within the sleep device, wherein the plurality of sensors include a sound sensor to collect sound data, a weight sensor to collect weight data with respect to the infant when positioned within the sleep device, and a motion sensor; and an analysis unit configured to perform cry analyses that analyze the data collected by the plurality of sensors to identify cry behavior states and generate predictive response instructions that control stimulus outputs by the sleep device or a peripheral device to soothe and transition the infant from the cry behavior states, wherein, with respect to the cry analyzes, the analysis unit is configured to:

analyze the collected sound data corresponding to cries together with the weight data including comparison of weight collected over time to a current weight, generate predictive response instructions to cause one or both of the sleep device or peripheral device to output stimuli, the output stimuli comprising initiation or modification of one or more of: temperature control modulated by a temperature control device, motion of a platform of the sleep device modulated by a motor, sound output from a speaker, or lighting modulated by lights, compare changes to cry behavior state characteristics of respective cry behavior state determinations following execution of predictive response instructions, and output a notification to a user interface that the infant is hungry when a cry state analysis informed by the comparison of changes to cry behavior state characteristics following previous cry behavior state determinations indicates the infant is in a hungry cry behavior state indicative of a cry behavior state that will not be soothed by the output stimuli.

2. The system of claim 1, wherein the cry analysis further includes correlation of the sound data corresponding to the cries and weight data with additional non-sound data collected by the plurality of sensors selected from motion data, vitals data, environmental data, sleep cycle data, wake/sleep data, or combination thereof.

3. The system of claim 1, wherein the characteristics of the sound data analyzed includes amplitude, frequency, wavelength, duration, or combination thereof.

4. The system of claim 3, wherein the characteristics of the sound data analyzed includes sound patterns, cadence, or both.

5. The system of claim 3, wherein the cry analysis starts with a baseline cry to differentiate between cries and grunts.

6. The system of claim 1, wherein the sound analysis module is configured to generate a cry algorithm that is personalized to the infant and use the cry algorithm in the cry analyses.

7. The system of claim 6, wherein the cry algorithm is configured to identify values or value ranges in measured characteristics based on previous analyses that are specific to the infant and its cry behavior states.

8. The system of claim 1, wherein the cry analysis further includes analysis of motion data, vital data, or combinations thereof collected by the plurality of sensors.

9. The system of claim 8, wherein the cry analysis includes the analysis of motion data collected by a motion sensor, and wherein the analysis of the motion data includes identification of intensity of kicking or other motions of the infant.

10. The system of claim 8, wherein, when the cry analysis identifies grunting in the sound data corresponding to the cries and determines if similar grunting sounds have been associated with one or more levels of hunger states, sleep states, tired states, content states, bored states, unwell states, or other behavioral states in previous cry analyses.

11. The system of claim 1, wherein the cry analysis further includes analysis of motion data collected by a motion sensor related to a movement of the infant during collection of the sound data corresponding to the cries, and wherein the movement corresponds to leg movement, eye movement, arm movement, body movement, or head movement.

12. The system of claim 11, wherein the analysis of the motion data includes analyzing rate, duration, pattern, and/or distance of the movement.

13. The system of claim 1, wherein the cry analysis is further configured to distinguish between whether the infant is unwell/ill, uncomfortable, content, bored, or tired.

14. The system of claim 1, wherein the cry analysis further includes analysis of motion data collected by the motion sensor related to a movement of the infant during collection of the sound data corresponding to the cries, and wherein the movement corresponds to movement of feet, toes, mouth, hands, or fingers.

15. The system of claim 1, wherein the notification includes a suggested amount or duration of feeding.

16. The system of claim 1, wherein the user interface is accessible to a user to specify a desired behavior state and the system is configured to provide a suggested feeding schedule along with one or more additional instructions to transition the infant to the desired behavioral state.

17. The system of claim 16, wherein the suggested feeding schedule includes an amount, duration, and timing of feeding to transition the infant to the desired behavioral state.

18. The system of claim 16, wherein the one or more additional instructions include a setting with respect to a sleep device and/or peripherals of the sleep device to transition the infant to the desired behavioral state.

19. The system of claim 1, wherein the comparison of changes to cry behavior state characteristics are taken from multiple time points after initiation of output stimuli.

20. The system of claim 1, wherein the comparison of changes to cry behavior state characteristics are taken from multiple ranges of time after initiation of output stimuli.

* * * * *